US009090535B2

(12) United States Patent
Riggs-Sauthier et al.

(10) Patent No.: US 9,090,535 B2
(45) Date of Patent: Jul. 28, 2015

(54) HYDROXYLATED TRICYCLIC COMPOUNDS

(75) Inventors: Jennifer Riggs-Sauthier, San Francisco, CA (US); Bo-Liang Deng, San Ramon, CA (US); Hema Gursahani, Foster City, CA (US)

(73) Assignee: Nektar Therapeutics, San Francisco, CA (US)

( * ) Notice: Subject to any disclaimer, the term of this patent is extended or adjusted under 35 U.S.C. 154(b) by 25 days.

(21) Appl. No.: 13/992,587

(22) PCT Filed: Dec. 9, 2011

(86) PCT No.: PCT/US2011/064223
§ 371 (c)(1),
(2), (4) Date: Aug. 13, 2013

(87) PCT Pub. No.: WO2012/079017
PCT Pub. Date: Jun. 14, 2012

(65) Prior Publication Data
US 2013/0317114 A1    Nov. 28, 2013

Related U.S. Application Data

(60) Provisional application No. 61/422,047, filed on Dec. 10, 2010.

(51) Int. Cl.
| C07C 217/52 | (2006.01) |
| C07C 217/54 | (2006.01) |
| A61K 31/137 | (2006.01) |
| A61P 25/08  | (2006.01) |
| A61P 25/24  | (2006.01) |

(52) U.S. Cl.
CPC ................................. *C07C 217/52* (2013.01)

(58) Field of Classification Search
CPC ... A61K 31/137; C07C 217/52; C07C 217/54
USPC .......................................... 514/654; 564/380
See application file for complete search history.

(56) References Cited

U.S. PATENT DOCUMENTS

| 2,554,736 A | 5/1951 | Haefliger et al. |
| 2,948,718 A | 8/1960 | Schindler |
| 3,177,209 A | 4/1965 | Holm |
| 3,205,264 A | 9/1965 | Tristram et al. |
| 3,244,748 A | 4/1966 | Tishler et al. |
| 3,271,451 A | 9/1966 | Tishler et al. |
| 3,299,139 A | 1/1967 | Pedersen |
| 3,312,689 A | 4/1967 | Schmutz et al. |
| 3,409,640 A | 11/1968 | Villani |
| 3,419,547 A | 12/1968 | Schmutz et al. |
| 3,438,981 A | 4/1969 | Stach |
| 3,442,949 A | 5/1969 | Wendler |
| 3,454,554 A | 7/1969 | Biel et al. |
| 3,467,650 A | 9/1969 | Schindler et al. |
| 3,527,766 A | 9/1970 | Protiva et al. |
| 3,574,852 A | 4/1971 | Dyrsting et al. |
| 3,622,565 A | 11/1971 | Fouche et al. |
| 3,627,832 A | 12/1971 | Schulenberg et al. |
| 3,637,660 A | 1/1972 | Eriksoo et al. |
| 3,663,696 A | 5/1972 | Howell et al. |
| 3,758,528 A | 9/1973 | Malen et al. |
| 3,963,778 A | 6/1976 | Schutz et al. |
| 7,786,133 B2 | 8/2010 | Bentley et al. |
| 8,569,380 B2 * | 10/2013 | Zhang et al. .................. 514/659 |
| 8,633,312 B2 | 1/2014 | Laufer et al. |

FOREIGN PATENT DOCUMENTS

| DE | 2030492 B2 | 10/1974 |
| GB | 1191800 A | 5/1970 |
| GB | 1252320 A | 11/1971 |
| WO | WO 02/098949 A1 | 12/2002 |
| WO | WO 2009/073154 * | 6/2009 ............. A61K 47/48 |
| WO | WO 2010/040843 A2 | 4/2010 |

OTHER PUBLICATIONS

Nordin et al., "Active Hydroxymetabolites of Antidepressants" Clin. Pharmacol.., 28 (1) 1995, 26-40.
Pollock et al., "Hydroxy Metabolites of Tricyclic Antidepressents: Evaluation of Relative Cardiotoxicity", Clin. Pharm/ Psych., 232-236, (1989).
Bertilsson et al., "Disposition of Single Oral Doses of E-10-hydroxynortriptyline in Health Subjects, with Some Observations on Pharmacodynamic Effects" Clin. Pharmacol., 1986, 261-267.
Crumb et al., "Comparison of $I_{to}$ in Young and Adult Human Atrial Myocytes: Evidence for Developmental Changes" Biophysical Journal, 57(3): 589 (1990).
Veronese et al., "PEGylation, successful approach to drug delivery", Drug Discovery Today, vol. 10, No. 21, 1451-1458, (2005).
Ertl et al., "Fast Calculation of Molecular Polar Surface Area as a Sum of Fragment-Based Contributions and Its Application to the Prediction of Drug Transport Properties" J. Med. Chem., 43, 3714-3717 (2000).

(Continued)

*Primary Examiner* — Sreeni Padmanabhan
*Assistant Examiner* — Irina Neagu

(57) ABSTRACT

The invention provides small molecule drugs that are chemically modified by covalent attachment of a water-soluble oligomer. A compound of the invention, when administered by any of a number of administration routes, exhibits characteristics that are different from the characteristics of the small molecule drug not attached to the water-soluble oligomer.

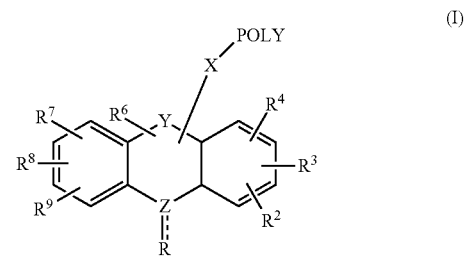

18 Claims, No Drawings

(56) References Cited

OTHER PUBLICATIONS

Kelder et al., "Polar Molecular Surface as a Dominating Determinant for Oral Absorption and Brain Penetration of Drugs" Pharm. Res., 16, (1999) 1514-1519.

Chen et al., "Synthesis and Properties of Aba Amphiphiles" J. Org. Chem., (1999) 6870-6873.

Kolesnikov et al., "Topical Opioids in Mice: Analgesia and Reversal of Tolerance by a Topical N-Methyl-D Aspartate Antagonist" J.Pharmacol. Exp. Ther (1999) 290:247-252.

Blair et al., "Roles of Tetrodotoxin—Sensitive Na+ Curren, TTX-Resistant Na+ Current, and Ca2+ Current in the Action Potentials of Nociceptive Sensory Neurons" J. Neurosci, (2002) 22: 10277-10290.

International Search Report and Written Opinion in PCT Application No. PCT/US2011/064223 mailed Mar. 5, 2012.

International Preliminary Report on Patentability in PCT Application No. PCT/US2011/064223 mailed Jun. 20, 2013.

Communication pursuant to Article 94(3) EPC in European Application No. 11 805 309.9-1462 dated Sep. 25, 2014.

Enzon Pharmaceuticals, Macromolecular Engineering Technologies, 16 pages, (2004).

NEKTAR™—Transforming Therapeutics, Nektar Molecule Engineering: Polyethylene Glycol and Derivatives for Advanced PEGylation, 24 pages, Catalog—2003, (Jul. 2003).

NEKTAR™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003—$1^{st}$, (Jan. 2003).

NOF Corporation, PEG Derivatives, Phospholipid and Drug Delivery Materials for Pharmaceuticals, 27 pages, Catalogue 2003—$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

* cited by examiner

HYDROXYLATED TRICYCLIC COMPOUNDS

CROSS REFERENCE TO RELATED APPLICATIONS

This application is a 35 U.S.C. §371 application of International Application No. PCT/US2011/064223, filed Dec. 9, 2011, designating the United States, which claims the benefit of priority under 35 U.S.C. §119(e) to U.S. Provisional Patent Application No. 61/422,047, filed Dec. 10, 2010, the disclosures of which are incorporated by reference in their entireties.

This invention comprises (among other things) chemically modified hydroxylated tricyclic compounds that possess certain advantages over tricyclics and hydroxylated tricyclics lacking the chemical modification. The chemically modified hydroxylated tricyclic compounds described herein relate to and/or have application(s) in (among others) the fields of drug discovery, pharmacotherapy, physiology, organic chemistry and polymer chemistry.

Clinical depression (also called major-depressive disorder or unipolar depression) is a common psychiatric disorder, characterized by a persistent lowering of mood, loss of interest in usual activities and diminished ability to experience pleasure.

While the term "depression" is commonly used to describe a temporary decreased mood, clinical depression is a serious illness that involves the body, mood, and thoughts and cannot simply be willed or wished away. It is often a disabling disease that affects a person's work, family and school life, sleeping and eating habits, general health and ability to enjoy life. The course of clinical depression varies widely: depression can be a once in a life-time event or have multiple recurrences, it can appear either gradually or suddenly, and either last for few months or be a life-long disorder. Having depression is a major risk factor for suicide; in addition, people with depression suffer from higher mortality from other causes. Clinical depression is usually treated by psychotherapy, antidepressants, or a combination of the two.

Neuropathy is a disease of the peripheral nerve or nerves. The four major forms of nerve damage are polyneuropathy, autonomic neuropathy, mononeuropathy, and mononeuritis multiplex. A more common form is peripheral polyneuropathy, which mainly affects the feet and legs. There are other less common forms of neuropathy, for example enteric neuropathy.

Aside from diabetes (i.e., diabetic neuropathy), the common causes of neuropathy are herpes zoster infection, HIV-AIDS, toxins, alcoholism, chronic trauma (such as repetitive motion disorders) or acute trauma (including surgery), neurotoxicity and autoimmune conditions such as celiac disease. Neuropathic pain is common in cancer as a direct result of the cancer on peripheral nerves (e.g., compression by a tumor), as a side effect of many chemotherapy drugs, and as a result of electrical injury. In many cases the neuropathy is "idiopathic," meaning no cause is found.

Neuropathic pain is usually perceived as a steady burning and/or "pins and needles" and/or "electric shock" sensations and/or tickling. The difference is due to the fact that "ordinary" pain stimulates only pain nerves, while a neuropathy often results in the firing of both pain and non-pain (touch, warm, cool) sensory nerves in the same area, producing signals that the spinal cord and brain do not normally expect to receive.

Neuropathic pain may be difficult to treat. A systematic review of randomized controlled trials found that the best treatments are tricyclics, anticonvulsants, and capsaicin. Tricyclic antidepressants (TCAs) are used in numerous applications; mainly indicated for the treatment of clinical depression, neuropathic pain, nocturnal enuresis, and ADHD, but they have also been used successfully for headache (including migraine headache), anxiety, insomnia, smoking cessation, bulimia nervosa, irritable bowel syndrome, narcolepsy, pathological crying or laughing, persistent hiccups, interstitial cystitis, and ciguatera poisoning, and as an adjunct in schizophrenia.

It is generally thought that tricyclic antidepressants work by inhibiting the re-uptake of the neurotransmitters norepinephrine, dopamine, or serotonin by nerve cells. Tricyclics may also possess affinity for muscarinic and histamine H1 through H4 receptors to varying degrees. Although norepinephrine and dopamine are generally considered stimulatory neurotransmitters, tricyclic antidepressants also increase the effects on H1 histamine, and thus most have sedative effects and may also be useful as anti-histaminic compounds.

The utility of antidepressants and anticonvulsants has been limited by potential adverse effects on the central nervous system such as bad dreams, drowsiness, blurred vision, decreased gastro-intestinal mobility and secretion, difficulty with urination, hyperthermia, and dry mouth. Additionally, the FDA has issued "black box" warnings for all antidepressant medications, including tricyclic antidepressants for increased suicidal behavior. As a consequence, pharmacotherapy with tricyclics would be improved if these and/or other side effects associated with their use could be decreased. Thus, there is a large unmet need for developing novel tricyclic compounds.

It has been reported that the metabolism of tricyclic antidepressants results in the hydroxylation of the parent molecule. Further, the hydroxylated form of certain parent tricyclic molecules has been shown to retain activity while lessening side effects. C. Nordin (1995), *Clin. Pharmacokinet.*, vol. 28 (1), 26-40; B. Pollock and J. Ferral (1989), *Clin. Pharm. in Psychology: Molecular Studies to Clinical Reality*, Springer Verlag; and Bertilsson et al., (1986), Clin. Phamacol. Ther. Vol. 40, no. 3, 261-7. By means of example, E-10-hydroxynortriptyline (the major hydroxy metabolite of nortriptyline and amitriptyline), has been shown to have activity as a norepinephrine reuptake inhibitor, while lessening the anticholinergic effects when compared to the parent molecule.

While hydroxylated metabolites of TCAs have shown activity, their natural formation in the body can be influenced by many factors, including the genetic makeup of the patient. As such, even for identical doses of a given TCA, the amount of hydroxylated metabolites generated by individual patients can vary significantly. Therefore, there is a need to better control the generation and amount of such metabolites so that their potential benefits as a therapeutic can be realized.

The present invention seeks to address these and other needs in the art.

In certain embodiments, a compound is provided, the compound comprising a hydroxylated tricyclic compound residue covalently attached via a stable or degradable linkage to a water-soluble, non-peptidic oligomer.

In certain embodiments, compounds of the invention include those of the formula:

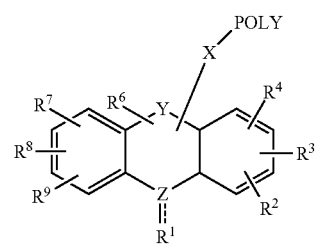

or at least one pharmaceutically acceptable salt thereof;

wherein:

Y is selected from —CH$_2$—, —CH—, —CH$_2$CH$_2$—, —CH=CH—, —CH$_2$—S—, CH$_2$—O—, —C(O)—CH$_2$—, CH$_2$—NH—, —S—CH$_2$—, —O—CH$_2$, —NH—CH$_2$—, —NH—S(O)$_2$—, —NH—C(O)—, —HN—, —O—, —N=C—, —C=N—, and —S—, each of which is independently optionally substituted;

Z is C or N;

R$^1$ is selected from alkyl, amino, acylamino, acyl, amido, aryloxy, alkylamino, dialkylamino wherein each alkyl group independently has from 1 to 6 carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl, each of which is independently optionally substituted;

each of R$^2$, R$^3$, R$^4$, R$^5$, R$^6$, R$^7$, R$^8$, and R$^9$, are independently selected from hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, each of which is independently optionally substituted;

X is an optional spacer moiety; and

POLY is a water-soluble, non-peptidic oligomer.

In certain embodiments, compounds of the invention include those having the following structure:

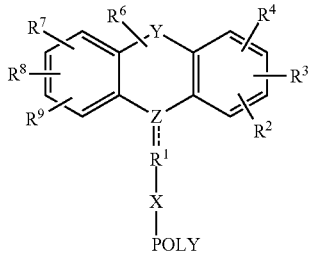

or at least one pharmaceutically acceptable salt thereof; wherein:

Y is selected from CH$_2$—, —CH—, —CH$_2$CH$_2$—, —CH=CH—, —CH$_2$—S—, CH$_2$—O—, —C(O)—CH$_2$—, CH$_2$—NH—, —S—CH$_2$—, —O—CH$_2$, —NH—CH$_2$—, —NH—S(O)$_2$—, —NH—C(O)—, —HN—, —O—, —N=C—, —C=N—, and —S—, each of which is independently optionally substituted;

Z is C or N;

R$^1$ is selected from alkyl, amino, acylamino, acyl, amido, aryloxy, alkylamino, dialkylamino wherein each alkyl group independently has from 1 to 6 carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl, each of which is independently optionally substituted;

each of R$^2$, R$^3$, R$^4$, R$^5$, R$^6$, R$^7$, R$^8$, and R$^9$, are independently selected from hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, each of which is independently optionally substituted;

X is an optional spacer moiety; and

POLY is a water-soluble, non-peptidic oligomer.

The "hydroxylated tricyclic residue" is a compound having a structure of a tricyclic compound that is altered by the presence of one or more bonds, which bonds serve to attach (either directly or indirectly) one or more water-soluble, non-peptidic oligomers. In certain embodiments, hydroxylated tricyclics have the structure

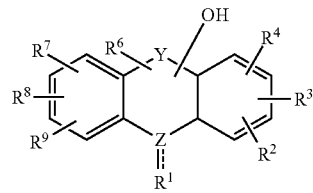

wherein:

Y is selected from —CH$_2$—, —CH—, —CH$_2$CH$_2$—, —CH=CH—, —CH$_2$—S—, CH$_2$—O—, —C(O)—CH$_2$—, CH$_2$—NH—, —S—CH$_2$—, —O—CH$_2$, —NH—CH$_2$—, —NH—S(O)$_2$—, —NH—C(O)—, —HN—, —O—, —N=C—, —C=N—, and —S—, each of which is independently optionally substituted;

Z is C or N;

R$^1$ is selected from the group consisting of alkyl, amino, acylamino, acyl, amido, aryloxy, alkylamino, dialkylamino wherein each alkyl group independently has from 1 to 6 carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl, each of which is independently optionally substituted; and each of R$^2$, R$^3$, R$^4$, R$^5$, R$^6$, R$^7$, R$^8$, and R$^9$, are independently selected from hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, each of which is independently optionally substituted.

In certain embodiments of the invention, a composition is provided, the composition comprising a compound comprising a hydroxylated tricyclic residue covalently attached via a stable or degradable linkage to a water-soluble and non-peptidic oligomer, and optionally, a pharmaceutically acceptable excipient.

In certain embodiments, a composition of matter is provided, the composition of matter comprising a compound comprising a hydroxylated tricyclic compound residue covalently attached via a stable or degradable linkage to a water-soluble, non-peptidic oligomer, wherein the compound is present in a dosage form.

In certain embodiments of the invention, a dosage form is provided, the dosage form comprising a compound comprising a hydroxylated tricyclic residue covalently attached via a stable or degradable linkage to a water-soluble, non-peptidic oligomer, wherein the compound is present in a unit dosage form.

In certain embodiments of the invention, a method is provided, the method comprising covalently attaching a water-soluble, non-peptidic oligomer to a hydroxylated tricyclic compound.

In certain embodiments of the invention, a method is provided, the method comprising administering a compound comprising a hydroxylated tricyclic residue covalently attached via a stable or degradable linkage to a water-soluble, non-peptidic oligomer.

These and other embodiments and features of the invention will become more fully apparent to one of ordinary skill in the art when read in conjunction with the following detailed description.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, in certain embodiments greater than 70% (by weight), and in certain embodiments greater than 95% (by weight) soluble, in water at room temperature. Typically, an unfiltered aqueous preparation of a "water-soluble" oligomer transmits at least 75%, in certain embodiments at least 95%, of the amount of light transmitted by the same solution after filtering. In certain embodiments the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. In certain embodiments oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from 1 to 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention may comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable "n" ranges from about 1 to 30, in certain embodiments from about 2 to about 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" and "terminally capped" are interchangeably used herein to refer to a terminal or endpoint of a polymer having an end-capping moiety. The end-capping moiety may comprise a hydroxy or $C_{1-20}$ alkoxy group, in certain embodiments a $C_{1-10}$ alkoxy group, and in certain embodiments a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. The end-capping moiety may include one or more atoms of the terminal monomer in the polymer [e.g., the end-capping moiety "methoxy" in $CH_3$—O—$(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane. The end-capping group can also comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like. Suitable detectors include photometers, films, spectrometers, and the like. The end-capping group can also comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

The term "targeting moiety" is used herein to refer to a molecular structure that helps the conjugates of the invention to localize to a targeting area, e.g., help enter, permeate, or penetrate a cell, or bind a receptor. In certain embodiments, the targeting moiety comprises of vitamin, cofactor, antibody, antigen, receptor, DNA, RNA, sialyl Lewis X antigen, hyaluronic acid, sugars, cell specific lectins, steroid or steroid derivative, RGD peptide, cell penetrating or cell targeting moiety, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched", in reference to the geometry or overall structure of an oligomer, refers to an oligomer having two or more polymer "arms" from a branch point.

"Forked", in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a bond, typically a covalent bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, in certain embodiments 97% or greater, in certain embodiments 98% or greater, in certain embodiments 99% or greater, and in certain embodiments 99.9% or greater.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000, if the oligomer were not attached to the moiety derived from a small molecule drug. A composition comprised of monodisperse conjugates may however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. In certain embodiments, for a bimodal oligomer composition as described herein, each peak is generally symmetric about its mean, although the size of the two peaks may differ. In certain embodiments, the polydispersity index of each peak in the bimodal distribution, Mw/Mn, is 1.01 or less, in certain embodiments 1.001 or less, and in certain embodiments 1.0005 or less, and in certain embodiments a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, in certain embodiments 1.001 or less and in certain embodiments 1.0005 or less, and in certain embodiments a MW/Mn value of 1.0000 if the oligomer were not attached to the moiety derived from a small molecule drug. A composition comprised of bimodal conjugates can include, however, one or more nonconjugate substances such as solvents, reagents, excipients, and so forth A "hydroxylated tricyclic" refers to an organic, inorganic, or organometallic compound typically having a molecular weight of less than about 1000 Daltons and having some degree of activity as a hydroxylated tricyclic therapeutic as described herein. As noted above, a hydroxylated tricyclic includes compounds of the formula

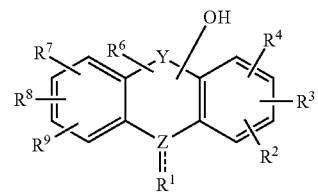

wherein $R^1$-$R^9$ and Y are as defined above. The location of the hydroxyl moiety may vary for each respective tricyclic. For example, tricyclics of the formula

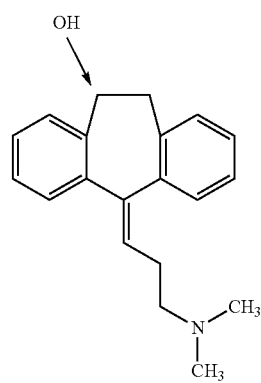 [SMILES: O ; CN(C)CCC=C1c2ccccc2CCc2ccccc21]

may exhibit hydroxylation at the 10 position, while compounds of the formula

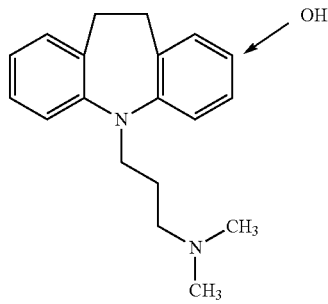 [SMILES: CN(C)CCCN1c2ccccc2CCc2ccccc21 ; O]

may exhibit hydroxylation at the 2 position. In certain embodiments, the hydroxylation may result in the formation of a chiral center. The present disclosure is understood to encompass mixtures of enantiomers, as well as, individual enantiomers.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

"Parent tricyclic" refers to the tricyclic molecule that, when hydroxylated, results in a hydroxylated tricyclic moiety disclosed herein.

A "biological membrane crossing rate," provides a measure of a compound's ability to cross a biological membrane (such as the blood-brain barrier (BBB)). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are described herein and/or in the relevant literature, and/or may be determined by one of ordinary skill in the art.

A "reduced metabolism" in reference to the present invention, refers to a measurable reduction in the rate and/or extent of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass metabolism," the same "reduced metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced metabolism" associated with the first pass metabolism and other metabolic processes are known, described herein and/or in the relevant literature, and/or may be determined by one of ordinary skill in the art. In certain embodiments, a conjugate of the invention may provide a reduced metabolism satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally. In certain embodiments, the a compound's bioavailability is greater than 25%, and in certain embodiments greater than 70%, where a compound's bioavailability is the fraction of administered drug that reaches the systemic circulation in unmetabolized form.

"Alkyl" refers to a hydrocarbon chain ranging from about 1 to 20 atoms in length. In certain embodiments, such hydrocarbon chains are saturated and may be branched or straight chain. In certain embodiments the hydrocarbon chains are straight. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are typically non-reactive with other functional groups contained within the molecule.

"Alkoxy" refers to an —O—R group, wherein R is alkyl or substituted alkyl, in certain embodiments $C_1$-$C_{20}$ alkyl (e.g., methoxy, ethoxy, propyloxy, etc.), and in certain embodiments $C_1$-$C_7$.

"Pharmaceutically acceptable excipient" or "pharmaceutically acceptable carrier" refers to component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

The terms "pharmaceutically acceptable salt" and "salts thereof" refer to acid addition salts or base addition salts of the compounds in the present invention. A pharmaceutically acceptable salt is any salt which retains the activity of the parent compound and does not impart any deleterious or undesirable effect on the subject to whom it is administered and in the context in which it is administered. Pharmaceutically acceptable salts include salts of both inorganic and organic acids. Pharmaceutically acceptable salts include acid salts such as acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic, toluenesulfonic, and the like. Other acceptable salts may be found, for example, in Stahl et al., *Pharmaceutical Salts: Properties, Selection, and Use*, Wiley-VCH; 1st edition (Jun. 15, 2002).

Where a salt is provided, it is understood that the salt may be converted to another salt or the free form of the compound, using techniques known to one of skill in the art.

As indicated above, the present invention is directed to (among other things) a compound comprising a hydroxylated tricyclic residue covalently attached via a stable or degradable linkage to a water-soluble, non-peptidic oligomer, or at least one pharmaceutically acceptable salt thereof.

As used herein, a bond which does not directly contact an atom in a molecule, indicates a substituent that may be present at any one of the available positions on the atoms of the molecule. For example, in the structure below, R may be present and any one of the atoms on the molecule by replacing an hydrogen on the particular atom:

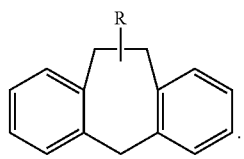

In certain embodiments the hydroxylated tricyclic compound residue is attached to the linker through the hydroxyl moiety.

In certain embodiments, the compound is a compound of the formula

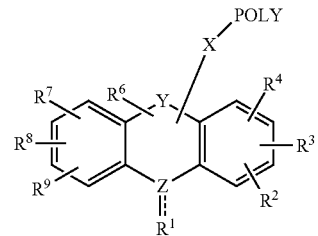

or at least one pharmaceutically acceptable salt thereof; wherein:
Y is selected from —CH$_2$—, —CH—, —CH$_2$CH$_2$—, —CH=CH—, —CH$_2$—S—, CH$_2$—O—, —C(O)—CH$_2$—, CH$_2$—NH—, —S—CH$_2$—, —O—CH$_2$, —NH—CH$_2$—, —NH—S(O)$_2$—, —NH—C(O)—, —HN—, —O—, —N=C—, —C=N—, and —S—, each of which is independently optionally substituted;
Z is C or N; and
R$^1$ is selected from alkyl, amino, acylamino, acyl, amido, aryloxy, alkylamino, dialkylamino wherein each alkyl group independently has from 1 to 6 carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl, each of which is independently optionally substituted;
each of R$^2$, R$^3$, R$^4$, R$^5$, R$^6$, R$^7$, R$^8$, and R$^9$, are independently selected from hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, each of which is independently optionally substituted;
X is an optional spacer moiety; and
POLY is a water-soluble, non-peptidic oligomer.
As used herein, the structure ═══ represents a bond, which may be selected from a single bond or a double bond.
In certain embodiments, Y is —CH$_2$CH$_2$—.
In certain embodiments, the compound is a compound of the formula

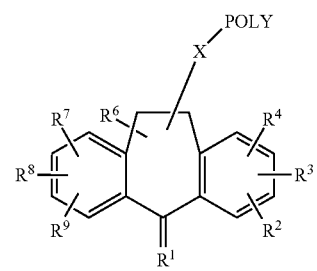

or at least one pharmaceutically acceptable salt thereof; wherein:
each of R$^2$, R$^3$, R$^4$, R$^5$, R$^6$, R$^7$, R$^8$, and R$^9$, are independently selected from hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, each of which is independently optionally substituted;
X is an optional spacer moiety; and
POLY is a water-soluble, non-peptidic oligomer.

In certain embodiments, the compound is a compound of the formula

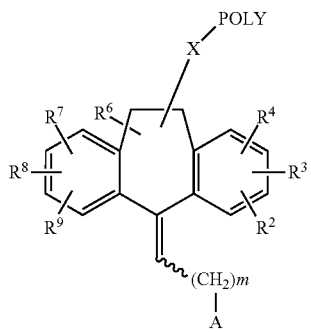

or at least one pharmaceutically acceptable salt thereof;
wherein:
each of $R^2$, $R^3$, $R^4$, $R^5$, $R^6$, $R^7$, $R^8$, and $R^9$, are independently selected from hydrogen, halo, cyano, hydroxy, carboxy, amino, acylamino, acyl, amido, aryloxy, alkyl, heteroalkyl, haloalkyl, alkoxy, and aryl, each of which is independently optionally substituted;
m is an integer from 1 to 4;
A is selected from amino, alkyl amino wherein the alkyl is lower alkyl, dialkylamino wherein each alkyl is lower alkyl, N-piperidino-, N-morpholino-, and N-pyrrolidino;
X is an optional spacer moiety; and
POLY is a water-soluble, non-peptidic oligomer.

In certain embodiments A is selected from amino, alkyl amino wherein the alkyl is lower alkyl, dialkylamino wherein each alkyl is lower alkyl.

In certain embodiments, A is selected from —NCH$_3$ and —N(CH$_3$)$_2$.

In certain embodiments, the water-soluble, non-peptidic oligomer is a poly(alkylene oxide).

In certain embodiments, the poly(alkylene oxide) is a poly(ethylene oxide).

In certain embodiments, the water-soluble, non-peptidic oligomer is made of 1 to 30 monomers.

In certain embodiments, the water-soluble, non-peptidic oligomer is made of 1 to 10 monomers.

In certain embodiments, the water-soluble, non-peptidic oligomer is made of 1 to 10 monomers.

In certain embodiments, the poly(alkylene oxide) includes an alkoxy or hydroxy end-capping moiety.

In certain embodiments, the compound is a compound of the formula:

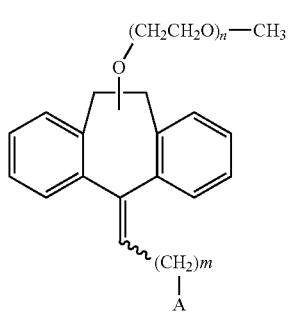

or at least one pharmaceutically acceptable salt thereof;
wherein:
n is an integer from 1 to 30;
m is an integer from 1 to 4; and
A is selected from amino, alkyl amino wherein the alkyl is lower alkyl, dialkylamino wherein each alkyl is lower alkyl.

In certain embodiments, m is 2.

In certain embodiments, the compound is a compound of the formula:

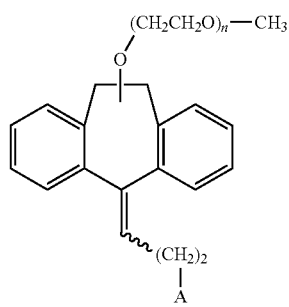

or at least one pharmaceutically acceptable salt thereof;
wherein A is —N(CH3)$_2$ and n is an integer from 1 to 30.

In certain embodiments, the compound is a compound of the formula:

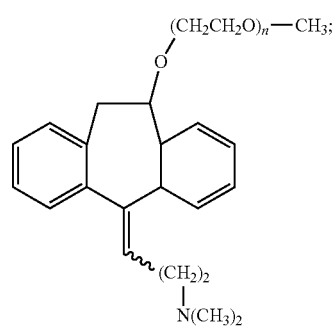

or at least one pharmaceutically acceptable salt thereof;
wherein n is an integer from 1 to 30.

In certain embodiments, the compound is a compound of the formula:

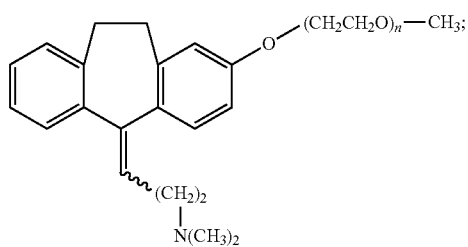

or at least one pharmaceutically acceptable salt thereof;
wherein n is an integer from 1 to 30.

In certain embodiments, the compound is a compound of the formula:

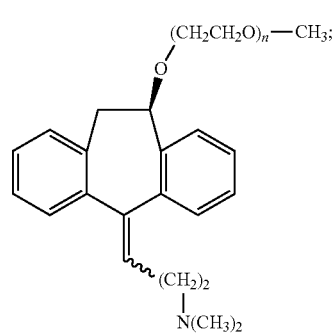

or at least one pharmaceutically acceptable salt thereof;
wherein n is an integer from 1 to 30.

In certain embodiments, the compound is a compound of the formula:

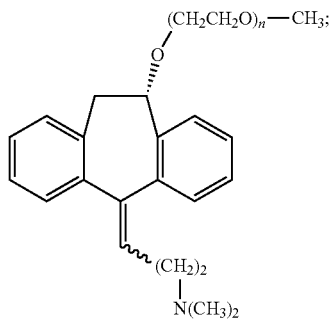

or at least one pharmaceutically acceptable salt thereof; wherein n is an integer from 1 to 30.

In certain embodiments, the compound is the (E) isomer.
In certain embodiments, the compound is the (Z) isomer.
In certain embodiments, n is an integer from 1 to 10.
In certain embodiments, n is an integer from 1 to 6. In certain embodiments, n is an integer from 2 to 6.

In certain embodiments, a compound, or at least one pharmaceutically acceptable salt thereof, selected from:
(R)-5-(3-dimethylamino-propylidene)-10-OmPEG$_4$-10,11-dihydro-5H-dibenzo[a,d]cyclohept-E-ene;
(R)-5-(3-dimethylamino-propylidene)-10-OmPEG$_1$-10,11-dihydro-5H-dibenzo[a,d]cyclohept-E-ene;
(R)-5-(3-dimethylamino-propylidene)-10-OmPEG$_2$-10,11-dihydro-5H-dibenzo[a,d]cyclohept-E-ene;
(R)-5-(3-dimethylamino-propylidene)-10-OmPEG$_6$-10,11-dihydro-5H-dibenzo[a,d]cyclohept-E-ene;
(R)-5-(3-dimethylamino-propylidene)-10-OmPEG$_8$-10,11-dihydro-5H-dibenzo[a,d]cyclohept-E-ene;
(S)-5-(3-dimethylamino-propylidene)-10-OmPEG$_4$-10,11-dihydro-5H-dibenzo[a,d]cyclohept-E-ene;
(S)-5-(3-dimethylamino-propylidene)-10-OmPEG$_6$-10,11-dihydro-5H-dibenzo[a,d]cyclohept-E-ene;
(S)-5-(3-dimethylamino-propylidene)-10-OmPEG$_8$-10,11-dihydro-5H-dibenzo[a,d]cyclohept-E-ene;
(R)-5-(3-dimethylamino-propylidene)-10-OmPEG$_4$-10,11-dihydro-5H-dibenzo[a,d]cyclohept-Z-ene;
(R)-5-(3-dimethylamino-propylidene)-10-OmPEG$_6$-10,11-dihydro-5H-dibenzo[a,d]cyclohept-Z-ene;
(R)-5-(3-dimethylamino-propylidene)-10-OmPEG$_8$-10,11-dihydro-5H-dibenzo[a,d]cyclohept-Z-ene;
(S)-5-(3-dimethylamino-propylidene)-10-OmPEG$_4$-10,11-dihydro-5H-dibenzo[a,d]cyclohept-Z-ene;
(S)-5-(3-dimethylamino-propylidene)-10-OmPEG$_6$-10,11-dihydro-5H-dibenzo[a,d]cyclohept-Z-ene;
(S)-5-(3-dimethylamino-propylidene)-10-OmPEG$_8$-10,11-dihydro-5H-dibenzo[a,d]cyclohept-Z-ene;
5-(3-Dimethylamino-propylidene)-10,11-dihydro-5H-dibenzo[a,d]cyclohept-E-en-2-mPEG$_4$;
5-(3-Dimethylamino-propylidene)-10,11-dihydro-5H-dibenzo[a,d]cyclohept-Z-en-2-mPEG$_4$;
5-(3-Dimethylamino-propylidene)-10,11-dihydro-5H-dibenzo[a,d]cyclohept-E-en-2-mPEG$_6$;
5-(3-Dimethylamino-propylidene)-10,11-dihydro-5H-dibenzo[a,d]cyclohept-Z-en-2-mPEG$_6$;
5-(3-Dimethylamino-propylidene)-10,11-dihydro-5H-dibenzo[a,d]cyclohept-E-en-2-mPEG$_8$; and
5-(3-Dimethylamino-propylidene)-10,11-dihydro-5H-dibenzo[a,d]cyclohept-Z-en-2-mPEG$_8$; is provided.

In certain embodiments, the compound is a compound of the formula

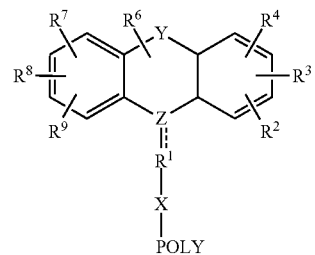

or at least one pharmaceutically acceptable salt thereof; wherein:
Y is selected from —CH$_2$—, —CH—, —CH$_2$CH$_2$—, —CH═CH—, —CH$_2$—S—, CH$_2$—O—, —C(O)—CH$_2$—, CH$_2$—NH—, —S—CH$_2$—, —O—CH$_2$, —NH—CH$_2$—, —NH—S(O)$_2$—, —NH—C(O)—, —HN—, —O—, —N═C—, —C═N—, and —S—, each of which is independently optionally substituted;
Z is C or N;
$R^1$ is selected from alkyl, amino, acylamino, acyl, amido, aryloxy, alkylamino, dialkylamino wherein each alkyl group independently has from 1 to 6 carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl, each of which is independently optionally substituted; and
each of $R^2$, $R^3$, $R^4$, $R^5$, $R^6$, $R^7$, $R^8$, and $R^9$, are independently selected from hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, each of which is independently optionally substituted; provided at least one of $R^2$, $R^3$, $R^4$, $R^5$, $R^6$, $R^7$, $R^8$, and $R^9$ is a hydroxyl group;
X is an optional spacer moiety; and POLY is a water-soluble, non-peptidic oligomer.

In certain embodiments, the compound is a compound of the formula:

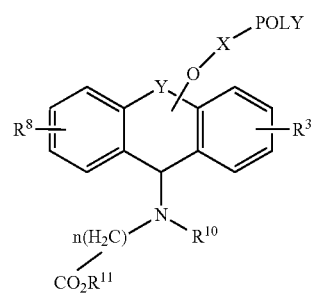

or at least one pharmaceutically acceptable salt thereof; wherein:
Y is a bridge selected from —(CH$_2$)$_m$— and —CH═CH—;
m is an integer of from 1 to 2;
$R^3$ and $R^8$ are each independently selected from hydrogen and halogen;
$R^{10}$ and $R^{11}$ are each independently selected from hydrogen and lower alkyl;

n is an integer of from 1 to 12;

X is an optional spacer moiety; and

POLY is a water-soluble, non-peptidic oligomer.

In certain embodiments, the compound is a compound of the formula:

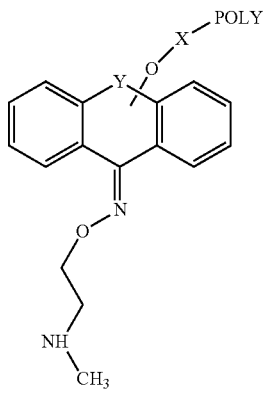

or at least one pharmaceutically acceptable salt thereof;

wherein Y is a bridge selected from —(CH$_2$)$_m$— and —CH=CH—; m is an integer of from 1 to 2; X is an optional spacer moiety; and POLY is a water-soluble, non-peptidic oligomer.

In certain embodiments, the compound residue is a compound of the formula:

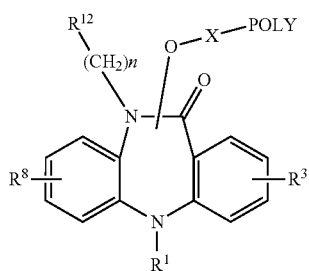

or at least one pharmaceutically acceptable salt thereof;

wherein:

$R^1$ is selected from hydrogen, methyl, and ethyl;

n is 2 or 3;

$R^3$ is selected from hydrogen, chloro, methyl, ethyl, methoxy, ethoxy, trifluoromethyl, methylmercapto, and ethylmercapto;

$R^8$ is selected from hydrogen, chloro, methyl, ethyl, methoxy, ethoxy, trifluoromethyl, methylmercapto, and ethylmercapto;

$R^{12}$ is selected from dialkylamino wherein each alkyl independently has 2 to 4 carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl;

X is an optional spacer moiety; and

POLY is a water-soluble, non-peptidic oligomer.

In certain embodiments, the compound is a compound of the formula:

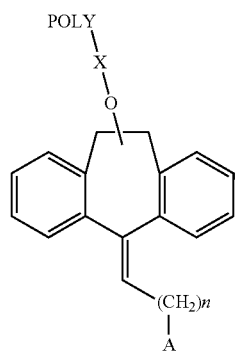

or at least one pharmaceutically acceptable salt thereof;

wherein:

n is an integer from 1 to 3; and

A is selected from amino, alkyl amino wherein the alkyl is lower alkyl, dialkylamino wherein each alkyl is lower alkyl, N-piperidino-, N-morpholino-, and N-pyrrolidino;

X is an optional spacer moiety; and

POLY is a water-soluble, non-peptidic oligomer.

In certain embodiments, the compound is a compound of the formula:

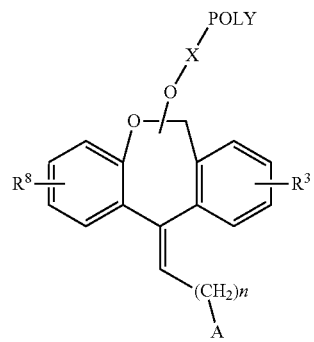

or at least one pharmaceutically acceptable salt thereof;

wherein:

$R^3$ and $R^8$ are each independently selected from hydrogen and halo;

n is an integer from 1 to 3;

A is selected from 4-(β-hydroxyethyl-piperidino) and —NR$^{13}$R$^{14}$ wherein R$^{13}$ and R$^{14}$ are each independently selected from hydrogen and lower alkyl;

X is an optional spacer moiety; and

POLY is a water-soluble, non-peptidic oligomer.

In certain embodiments, the compound is a compound of the formula:

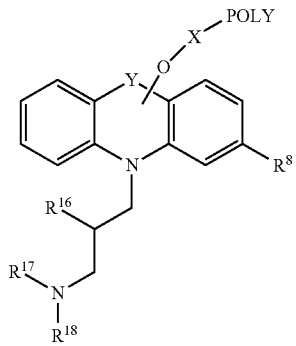

or at least one pharmaceutically acceptable salt thereof; wherein:

Y is selected from $CH_2$—$CH_2$ and CH=CH;

$R^8$ is selected from H, F, Cl, methoxy, $CF_3$, and $SO_2N(CH_3)_2$;

$R^{16}$ is selected from hydrogen and lower alkyl;

$R^{17}$ is lower alkyl;

$R^{18}$ is selected from lower alkyl and —$(CH_2)_nCOR^{19}$, wherein n is an integer from 1 to 3 and $R^{19}$ is an selected from phenyl and phenyl substituted with one to three substituents independently selected from F, Cl, OH, $CF_3$, lower alkyl and lower alkoxy; and a phenyl group having at the 3,4-positions a substituent selected from alkylidenedioxy (having a maximum of 6 carbon atoms), cycloalkylidenedioxy (having a maximum of 6 carbon atoms), and ethylenedioxy; or $R^{17}$ and $R^{18}$, taken together, form an optionally substituted heterocycle.

X is an optional spacer moiety; and

POLY is a water-soluble, non-peptidic oligomer.

In certain embodiments, the compound is a compound of the formula:

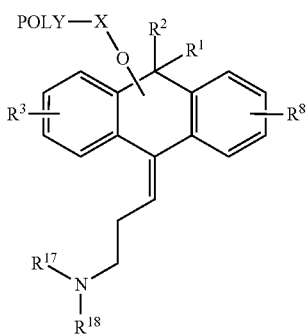

or at least one pharmaceutically acceptable salt thereof; wherein:

each of $R^1$ and $R^2$ is a lower-alkyl group; $R^3$ is selected from hydrogen, halo, lower-alkyl and lower-alkoxy; $R^8$ is selected from hydrogen, halo, lower-alkyl and lower-alkoxy;

$R^{17}$ is selected from hydrogen and lower alkyl;

$R^{18}$ is selected from hydrogen and lower alkyl;

X is an optional spacer moiety; and

POLY is a water-soluble, non-peptidic oligomer.

In certain embodiments, the compound is a compound of the formula:

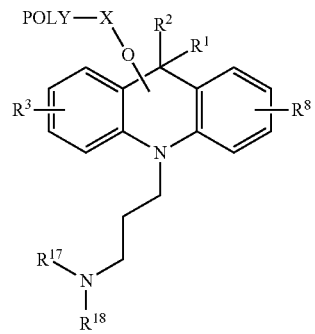

or at least one pharmaceutically acceptable salt thereof; wherein:

each of $R^1$ and $R^2$ is a lower-alkyl group; $R^3$ is selected from hydrogen, halo, lower-alkyl and lower-alkoxy; $R^8$ is selected from hydrogen, halo, lower-alkyl and lower-alkoxy;

$R^{17}$ is selected from hydrogen and lower alkyl;

$R^{18}$ is selected from hydrogen and lower alkyl;

X is an optional spacer moiety; and

POLY is a water-soluble, non-peptidic oligomer.

In certain embodiments, the compound is a compound of the formula:

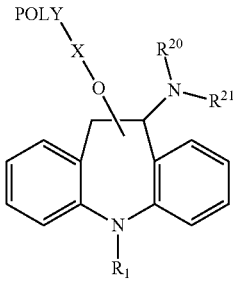

or at least one pharmaceutically acceptable salt thereof; wherein:

$R^{20}$ and $R^{21}$ are selected from hydrogen and lower alkyl;

$R^1$ is selected from hydrogen, lower alkyl, and benzyl.

X is an optional spacer moiety; and

POLY is a water-soluble, non-peptidic oligomer.

In certain embodiments, the compound is a compound of the formula:

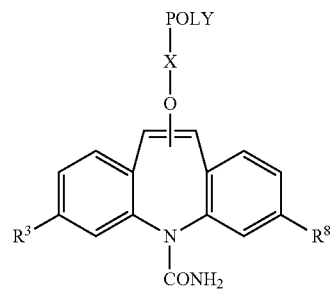

or at least one pharmaceutically acceptable salt thereof; wherein:

$R^3$ and $R^8$ are independently selected from hydrogen and halo;

X is an optional spacer moiety; and

POLY is a water-soluble, non-peptidic oligomer.

In certain embodiments, the compound is a compound of the formula:

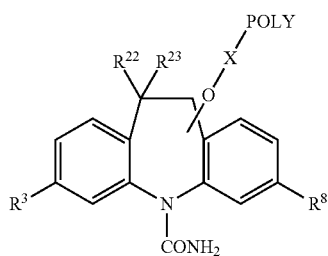

or at least one pharmaceutically acceptable salt thereof;
wherein:

$R^3$ and $R^8$ are independently selected from hydrogen and halo;

$R^{22}$ and $R^{23}$ are each independently selected from hydrogen, hydroxyl, alkoxy, and acyloxy; or $R^{22}$ and $R^{23}$ may together form a carbonyl X is an optional spacer moiety; and POLY is a water-soluble, non-peptidic oligomer.

In certain embodiments, the compound is a compound of the formula:

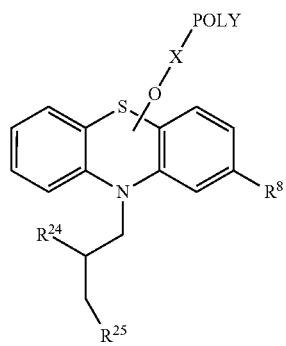

or at least one pharmaceutically acceptable salt thereof;
wherein:

$R^8$ is selected from hydrogen and halo;

$R^{24}$ is selected from hydrogen and —$NR^{17}R^{18}$ wherein $R^{17}$ is selected from hydrogen and lower alkyl; and $R^{18}$ is selected from hydrogen and lower alkyl;

$R^{25}$ is selected from hydrogen and —$NR^{17}R^{18}$ wherein $R^{17}$ is selected from hydrogen and lower alkyl; and $R^{18}$ is selected from hydrogen and lower alkyl;

X is an optional spacer moiety; and

POLY is a water-soluble, non-peptidic oligomer.

In certain embodiments, the hydroxylated tricyclic compound residue is a hydroxylated residue of a parent tricyclic selected from amineptine, amitriptyline, amitriptylinoxide, amoxapine, butriptyline, clomiprimine, demexiptiline, desipramine, dibenzepin, dimetacrine, dothiepin, doxepin, fluacizine, imipramine, imipramine N-oxide, lofepramine, melitracen, metapramine, mirtazapine, nortriptyline, opipramol, propizepine, protriptyline, quinupramine, tianeptine, trimipramine, carbamazepine, oxcarbazepine, eslicarbazepine acetate, chlorpromazine, promethazine, clozapine, loxapine, and eslicarbazepine.

In certain embodiments, the hydroxylated tricyclic compound residue is 10-OH nortriptyline. In certain embodiments, the hydroxylated tricyclic compound residue is E-10-OH nortriptyline. In certain embodiments, the hydroxylated tricyclic compound residue is 10-OH amitriptyline. In certain embodiments, the hydroxylated tricyclic compound residue is E-10-OH amitriptyline.

In certain embodiments, the hydroxylated tricyclic compound residue is a residue of a hydroxylated tricyclic compound having the structure

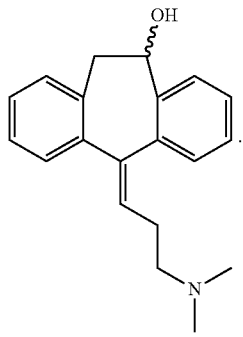 [SMILES: CN(C)CC/C=C1/c2ccccc2CC(O)c2ccccc21]

In certain embodiments, the hydroxylated tricyclic compound residue is a residue of a hydroxylated tricyclic compound having the structure

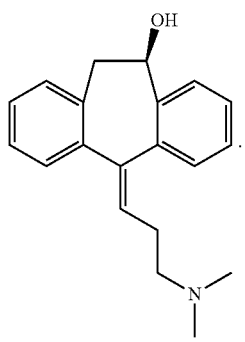 [SMILES: CN(C)CC/C=C1/c2ccccc2C[C@@H](O)c2ccccc21]

In certain embodiments, the water-soluble, non-peptidic oligomer is a poly(alkylene oxide).

In certain embodiments, the poly(alkylene oxide) is a poly(ethylene oxide).

In certain embodiments, the water-soluble, non-peptidic oligomer is made of 1 to 30 monomers.

In certain embodiments, the water-soluble, non-peptidic oligomer is made of 1 to 10 monomers. In certain embodiments, the water-soluble, non-peptidic oligomer is made of 1 to 6 monomers. In certain embodiments, the water-soluble, non-peptidic oligomer is made of 2 to 6 monomers.

In certain embodiments, the poly(alkylene oxide) includes an alkoxy, methyl, or hydroxy end-capping moiety.

In certain embodiments, a single water-soluble, non-peptidic oligomer is attached to the hydroxylated tricyclic compound residue.

In certain embodiments, more than one water-soluble, non-peptidic oligomer is attached to the hydroxylated tricyclic compound residue.

In certain embodiments, the hydroxylated tricyclic compound residue is covalently attached via a stable linkage.

In certain embodiments, the hydroxylated tricyclic compound residue is covalently attached via a degradable linkage.

In certain embodiments, the linkage is an ether linkage.

In certain embodiments, the linkage is an ester linkage.

It is believed that an advantage of the compounds of the present invention is their ability to retain some degree of hydroxylated tricyclic activity while also exhibiting a decrease in metabolism. Although not wishing to be bound by theory, it is believed that the hydroxylated tricyclic residue- and oligomer-containing compounds described herein—in contrast to the oligomer-free "original" hydroxylated tricyclic structure—are not metabolized as readily because the oligomer serves to reduce the overall affinity of the compound to substrates that may metabolize tricyclics. In addition (and again, not wishing to be bound by theory), the extra size introduced by the oligomer—in contrast to the oligomer-free "original" hydroxylated tricyclic structure—reduces the ability of the compound to cross the blood-brain barrier. Even should the linkage between the residue of the hydroxylated tricyclic and the oligomer be degradable, the compound still offers advantages (such as avoiding first-pass metabolism upon initial absorption).

Use of discrete oligomers (e.g., from a monodisperse or bimodal composition of oligomers, in contrast to relatively impure compositions) to form oligomer-containing compounds may alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. In certain embodiments the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatography with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble, non-peptidic oligomer-small molecule drug conjugate exhibits a blood-brain barrier crossing rate that is reduced as compared to the crossing rate of the small molecule drug not attached to the water-soluble, non-peptidic oligomer. Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. In certain embodiments, a reduction in the blood-brain barrier crossing rate for a conjugate of the invention is at least about 20%.

As indicated above, the compounds of the invention include a tricyclic residue. Assays for determining whether a given compound (regardless of whether the compound includes a water-soluble, non-peptidic oligomer or not) can act as an antidepressant, anticonvulsant, or as an analgesic are described infra.

The variables, notations, and symbols used in the following paragraphs with respect to formula may not relate to other paragraphs. Therefore, definitions of the notations and symbols in each paragraph are normally limited to it and should not be used to construe other paragraphs, unless indicated otherwise.

In some instances, the parent tricyclics and/or the hydroxylated tricyclic can be obtained from commercial sources. In addition, the parent tricyclics and/or the hydroxylated tricyclic can be obtained through chemical synthesis. Examples of tricyclics as well as synthetic approaches for preparing tricyclics are described in the literature and in, for example, DE2030492A1, DE2030492A, DE2030492B2, DE2030492C3, GB1191800A, U.S. Pat. No. 2,554,736, U.S. Pat. No. 2,948,718, U.S. Pat. No. 3,177,209, U.S. Pat. No. 3,205,264, U.S. Pat. No. 3,244,748, U.S. Pat. No. 3,271,451, U.S. Pat. No. 3,299,139, U.S. Pat. No. 3,312,689, U.S. Pat. No. 3,409,640, U.S. Pat. No. 3,419,547, U.S. Pat. No. 3,438,981, U.S. Pat. No. 3,442,949, U.S. Pat. No. 3,454,554, U.S. Pat. No. 3,467,650, U.S. Pat. No. 3,527,766, U.S. Pat. No. 3,574,852, U.S. Pat. No. 3,622,565, U.S. Pat. No. 3,637,660, U.S. Pat. No. 3,663,696, U.S. Pat. No. 3,758,528, U.S. Pat. No. 3,963,778. Each of these (and other) tricyclics can be covalently attached (either directly or through one or more atoms) to a water-soluble and non-peptidic oligomer. Additionally, each of these tricyclics can be converted to a hydroxylated tricyclic.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety. The tricyclic for coupling to a water-soluble, non-peptidic oligomer possesses a free hydroxyl, carboxyl, thio, amino group, or the like (i.e., "handle") suitable for covalent attachment to the oligomer. In addition, the tricyclic may be modified by introduction of a reactive group, preferably by conversion of one of its existing functional groups to a functional group suitable for formation of a stable covalent linkage between the oligomer and the drug.

Accordingly, each oligomer is composed of up to three different monomer types selected from: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, alditol such as mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

In certain embodiments, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble and non-peptidic oligomer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: from about 1 to about 25; from about 1 to about 20; from about 1 to about 15; from about 1 to about 12; from about 1 to about 10; and from about 1 to about 6.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 59, 103, 147, 191, 235, 2279, 323, 367, 411, and 455 Daltons, respectively. When the oligomer has 11, 12, 13, 14, or 15 monomers, these values correspond to methoxy end-capped oligo(ethylene oxide) having molecular weights corresponding to about 499, 543, 587, 631, and 675 Daltons, respectively.

When the water-soluble, non-peptidic oligomer is attached to the tricyclic (in contrast to the step-wise addition of one or more monomers to effectively "grow" the oligomer onto the tricyclic), the composition containing an activated form of the water-soluble, non-peptidic oligomer may be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be tri-modal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

In certain embodiments, the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the tricyclic) may be a single bond, a single atom, such as an oxygen atom or a sulfur atom, two atoms, or a number of atoms. In certain embodiments, the spacer moiety is linear in nature. The spacer moiety, "X," is hydrolytically stable, and in certain embodiments, enzymatically stable. In certain embodiments, the spacer moiety "X" is one having a chain length of less than about 12 atoms, and in certain embodiments less than about 10 atoms, and in certain embodiments less than about 8 atoms and in certain embodiments less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—$\underline{C}$(O)—NH—). In certain embodiments, the linkage does not comprise further spacer groups.

In certain embodiments, the spacer moiety "X" comprises an ether, amide, urethane, amine, thioether, urea, or a carbon-carbon bond. Functional groups such as those discussed below, and illustrated in the examples, are typically used for forming the linkages. In certain embodiments, the spacer moiety also comprises (or be adjacent to or flanked by) other atoms, as described further below.

More specifically, in certain embodiments, a spacer moiety of the invention, X, may be any of the following: "—" (i.e., a covalent bond, that may be stable or degradable, between the tricyclic residue and the water-soluble, non-peptidic oligomer), —O—, —NH—, —S—, —C(O)—, —C(O)O—, —OC(O)—, —CH₂—C(O)O—, —CH₂—OC(O)—, —C(O)O—CH₂—, —OC(O)—CH₂—, C(O)—NH, NH—C(O)—NH, O—C(O)—NH, —C(S)—, —CH₂—, —CH₂—CH₂—, —CH₂—CH₂—CH₂—, —CH₂—CH₂—CH₂—CH₂—, —O—CH₂—, —CH₂—O—, —O—CH₂—CH₂—, —CH₂—O—CH₂—, —CH₂—CH₂—O—, —O—CH₂—CH₂—CH₂—, —CH₂—O—CH₂—CH₂—, —CH₂—CH₂—O—CH₂—, —CH₂—CH₂—CH₂—O—, —O—CH₂—CH₂—CH₂—, —CH₂—O—CH₂—CH₂—CH₂—, —CH₂—CH₂—O—CH₂—CH₂—, —CH₂—CH₂—CH₂—O—CH₂—, —CH₂—CH₂—CH₂—CH₂—O—, —C(O)—NH—CH₂—, —C(O)—NH—CH₂—CH₂—, —CH₂—C(O)—NH—CH₂—, —CH₂—CH₂—C(O)—NH—, —C(O)—NH—CH₂—CH₂—CH₂—, —CH₂—C(O)—NH—CH₂—CH₂—, —CH₂—CH₂—C(O)—NH—CH₂—, —CH₂—CH₂—CH₂—C(O)—NH—, —C(O)—NH—CH₂—CH₂—CH₂—CH₂—, —CH₂—C(O)—NH—CH₂—CH₂—CH₂—, —CH₂—CH₂—C(O)—NH—CH₂—CH₂—, —CH₂—CH₂—CH₂—C(O)—NH—CH₂—, —CH₂—CH₂—CH₂—C(O)—NH—CH₂—CH₂—, —CH₂—CH₂—CH₂—CH₂—C(O)—NH—, —CH₂—CH₂—CH₂—C(O)—NH—, —C(O)—NH—CH₂—, —CH₂—CH₂—CH₂—C(O)—NH—CH₂—CH₂—, —CH₂—CH₂—CH₂—C(O)—NH—CH₂—, —C(O)—NH—CH₂—, —CH₂—NH—C(O)—CH₂—, —CH₂—CH₂—NH—C(O)—, —NH—C(O)—CH₂—CH₂—, —CH₂—NH—C(O)—CH₂—CH₂, —CH₂—CH₂—NH—C(O)—CH₂—CH₂, —C(O)—NH—CH₂—, —C(O)—CH₂—NH—, —C(O)—NH—CH₂—CH₂—, —O—C(O)—NH—CH₂—, —O—C(O)—NH—CH₂—CH₂—, —NH—CH₂—, —NH—CH₂—CH₂—, —CH₂—NH—CH₂—, —CH₂—CH₂—NH—CH₂—, —C(O)—CH₂—, —C(O)—CH₂—CH₂—, —CH₂—C(O)—CH₂—, —CH₂—CH₂—C(O)—CH₂—, —CH₂—CH₂—C(O)—CH₂—CH₂—, —CH₂—CH₂—C(O)—, —CH₂—CH₂—CH₂—C(O)—NH—CH₂—CH₂—NH—, —CH₂—CH₂—CH₂—C(O)—NH—CH₂—CH₂—NH—C(O)—, —CH₂—CH₂—CH₂—C(O)—NH—CH₂—CH₂—NH—C(O)—CH₂—, bivalent cycloalkyl group, —N(R⁶)—, R⁶ is H or an organic radical selected from alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the tricyclic) with a corresponding functional group within the tricyclic. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

In certain embodiments, the water-soluble, non-peptidic oligomer is an oligomer bearing an aldehyde functional group. In this regard, the oligomer will have the following structure: CH₃O—(CH₂—CH₂—O), —(CH₂)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The termini of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. In certain embodiments, nucleophiles include amine, hydrazine, hydrazide, and thiol, and in certain embodiments amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Additional esters include imidazolyl esters and benzotriazole esters. Additional esters include propionic acid or butanoic acid esters, as described in co-owned U.S. Pat. No. 5,672,662. These include groups of the form —(CH$_2$)$_{2-3}$C(=O)O-Q, where Q is optionally selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to Bairn, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the tricyclic may not have a functional group suited for conjugation. In this instance, it is possible to modify (or "functionalize") the "original" tricyclic so that it does have a functional group suited for conjugation. For example, if the tricyclic has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule tricyclic bearing a carboxyl group wherein the carboxyl group-bearing small molecule tricyclic is coupled to an amino-terminated oligomeric ethylene glycol, to provide a conjugate having an amide group covalently linking the small molecule tricyclic to the oligomer. This can be performed, for example, by combining the carboxyl group-bearing small molecule tricyclic with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule tricyclic bearing a hydroxyl group wherein the hydroxyl group-bearing small molecule tricyclic is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

Further, it is possible to prepare a conjugate of a small molecule tricyclic moiety bearing a hydroxyl group (such as, for example, the tricyclic moieties having structures encompassed within Formula I) wherein the hydroxyl group-bearing small molecule tricyclic moiety is coupled to an oligomeric ethylene glycol bearing an haloformate group [e.g., CH$_3$(OCH$_2$CH$_2$)$_n$OC(O)-halo, where halo is chloro, bromo, iodo] to result in a carbonate [—O—C(O)—O—] linked small molecule conjugate. This can be performed, for example, by combining a tricyclic moiety and an oligomeric ethylene glycol bearing a haloformate group in the presence of a nucleophilic catalyst (such as 4-dimethylaminopyridine or "DMAP") to thereby result in the corresponding carbonate-linked conjugate.

In another example, it is possible to prepare a conjugate of a small molecule tricyclic bearing a ketone group by first reducing the ketone group to form the corresponding hydroxyl group. Thereafter, the small molecule tricyclic now bearing a hydroxyl group can be coupled as described herein.

In still another instance, it is possible to prepare a conjugate of a small molecule tricyclic bearing an amine group. In one approach, the amine group-bearing small molecule tricyclic and an aldehyde-bearing oligomer are dissolved in a suitable buffer after which a suitable reducing agent (e.g., $NaCNBH_3$) is added. Following reduction, the result is an amine linkage formed between the amine group of the amine group-containing small molecule tricyclic and the carbonyl carbon of the aldehyde-bearing oligomer.

In another approach for preparing a conjugate of a small molecule tricyclic bearing an amine group, a carboxylic acid-bearing oligomer and the amine group-bearing small molecule tricyclic are combined, typically in the presence of a coupling reagent (e.g., DCC). The result is an amide linkage formed between the amine group of the amine group-containing small molecule tricyclic and the carbonyl of the carboxylic acid-bearing oligomer.

The conjugates of the invention can exhibit a reduced blood-brain barrier crossing rate. Moreover, the conjugates maintain at least about 5%, 10%, 20%, 30%, 40%, 50%, 60%, 70%, or more of the bioactivity of the unmodified parent small molecule drug.

While it is believed that the full scope of the conjugates disclosed herein behave as described, an optimally sized oligomer can be identified as follows.

First, an oligomer obtained from a monodisperse or bimodal water soluble oligomer is conjugated to the small molecule drug. In certain embodiments, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. In certain embodiments, the compounds according to the invention maintain a significant degree of bioactivity relative to the parent drug, i.e., greater than about 30% of the bioactivity of the parent drug, in certain embodiments, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the tricyclic or the conjugate of a tricyclic and a water-soluble non-peptidic polymer has activity as a tricyclic therapeutic, it is possible to test such a compound. The tricyclic compounds have sedative, hypnotic, anti-anxiety, tranquilizing, anticonvulsant, and muscle relaxant effects in mammals and birds. They also exhibit anti-depressant and analgesic actions in mammals.

In vitro binding studies to receptors using various cell lines have become routine in pharmaceutical industry.

Sedative effects: Chimney test: The test determines the ability of mice to back up and out of a vertical glass cylinder within 30 seconds. At an effective dosage, 50% of the mice will fail doing it ($ED_{50}$).

Dish test: Mice in Petri dishes (10 cm diameter, 5 cm high, partially embedded in wood shavings), climb out in a very short time, when not treated. Mice remaining in the dish for more than 3 minutes indicate tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute. The $ED_{50}$ (intraperitoneal administration) is determined by identifying the amount of compound that causes 50% of the mice to stay on the pedestal.

Nicotine antagonism test: Mice in a group of 6 are injected with the test compound. Thirty minutes later the mice including control (untreated) mice are injected with nicotine salicylate (2 mg/kg). The control mice show over-stimulation, i.e., (1) running convulsions followed by (2) tonic extensor fits; followed by (3) death. The $ED_{50}$ (intraperitoneal administration) is determined by identifying the amount of compound that causes 50% of the mice to not show over-stimulation.

Antagonism to strychnine (as sulfate): The test consists of orally administering into mice the test compound, and 30 minutes later 3 mg/kg strychnine sulfate intraperitoneally. The survivors after 4 hours reflect the activity of the compound as a muscle relaxant and antispasmodic.

The main function of an anti-depressant is to return the depressed individual to normal functioning. This should be carefully differentiated from psychic stimulants such as the amphetamines which produce over-stimulation in the normal individual.

Many different methods have been and are used to evaluate antidepressant activity. In general these methods involve antagonism to a depressant such as reserpine or tetrabenazine or a synergistic increase of the toxicity of certain compounds (i.e. yohimbine or 3,4-dihydroxyphenylalanine) and comparison of the drug action of the new compound with other known antidepressants. No single test alone can determine whether or not a new compound is an antidepressant or not, but the profile evidenced by various tests will establish the anti-depressant action if present. A number of such tests are described below.

Hypothermic tests with oxotemiorine: [1-(4-pyrrolidino-2-butynyl)-2-pyrrolidinone]. Oxotremorine (as well as apomorphine and tetrabenazine) produces hypothermic responses in mice. This response is blocked by anticholinergics and antidepressants such as atropine and imipramine respectively. Mice are injected intraperitoneally with 1 mg of oxotremorine. The lowering of the body temperature is measured rectally with an electronic thermometer, before and 30 minutes after drug administration. About four degree centigrade difference between the control mice (oxotremorine alone) and the treated mice (oxotremorine and test compound) is used to indicate the antagonistic action of the test compound.

Potentiation of yohimbine aggregation toxicity: Mice are injected with the anti-depressant and 30 minutes later with 30 mg of yohimbine hydrochloride in saline solution. After two hours, the $LD_{50}$ are determined. Normally no mice are killed by 30 mg of yohimbine. If yohimbine is administered in the presence of an anti-depressant an increase of the toxicity of yohimbine is observed. The $ED_{50}$ value of the test compound is determined.

Potentiation of apomorphine gnawing: Mice are administered the test compound intraperitoneally one hour prior to the subcutaneous injection of apomorphine hydrochloride 10 mg/kg. The mice are then placed in a plastic box (6"×11"×5") lined at the bottom with a cellophane-backed, absorbent paper. The degree of damage to the paper at the end of 30 min is scored from zero to 4. The scores of 3 and 4 indicate that the compound is a potentiator of apomorphine in this test.

To determine whether the tricyclic derivative itself or the conjugate of tricyclic or a derivative thereof has activity (such as analgesic activity), it is possible to test such a compound. For example, the compound of interest can be administered to a mouse topically and analgesia assessed as described in Kolesnikov et al. (1999) J. Pharmacol. Exp. Ther. 290: 247-252. Briefly, the distal portion of the tail (2-3 cm) is immersed in a DMSO solution containing the compound of interest for the stated time, typically two minutes. Testing is performed on the portion of the tail immersed in the treatment solution, because the analgesic actions of agents administered in this manner are restricted to the exposed portions of the tail. Antinociception, or analgesia, is defined as a tail-flick latency for an individual animal that is twice its baseline latency or greater. Baseline latencies typically range from 2.5 to 3.0 seconds, with a maximum cutoff latency of 10 seconds to minimize tissue damage in analgesic animals. $ED_{50}$ values can be determined.

In another approach for evaluating analgesic activity of the tricyclic derivative itself or the conjugate of tricyclic or a derivative thereof, a "writhing test" can be conducted. Briefly, a 0.7% acetic acid solution is administered (i.p.) to a mouse and the numbers of writhing responses are counted for ten minutes. Thereafter, the compound to be tested is administered [by, for example, injection (e.g., subcutaneous injection)] to the mouse and antinociception is quantified as percent inhibition using the following formula: % inhibition= [(control responses-test responses)/control responses]×100.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, in certain embodiments from about 5%-98% by weight, in certain embodiments from about 15-95% by weight of the excipient, and in certain embodiments less than 30% by weight preferred.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. Exemplary preparations are in a form suitable for oral administration such as a tablet, caplet, capsule, gel cap, troche, dispersion, suspension, solution, elixir, syrup, lozenge, transdermal patch, spray, suppository, and powder.

Oral dosage forms for those conjugates that are orally active include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

In certain embodiments, the oral dosage form is a capsule in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In certain embodiments, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

In certain embodiments, conjugates of the present invention may exhibit a reduction in first pass metabolism relative to the parent drug. Such a result is useful for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. In certain embodiments reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism can be reduced), the conjugates are particularly useful when the small molecule drug is metabolized by a hepatic enzyme (e.g., one or more of the cytochrome P450 isoforms) and/or by one or more intestinal enzymes.

All articles, books, patents, patent publications and other publications referenced herein are incorporated by reference in their entireties. In the event of an inconsistency between the teachings of this specification and the art incorporated by reference, the meaning of the teachings in this specification shall prevail.

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data were generated by NMR spectrometers. A list of certain compounds as well as the source of the compounds is provided below.

EXAMPLE 1

Preparation of 10-hydroxy Amitriptyline Derivatives 10-hydroxy derivatives of amitriptyline were prepared based on the scheme below.

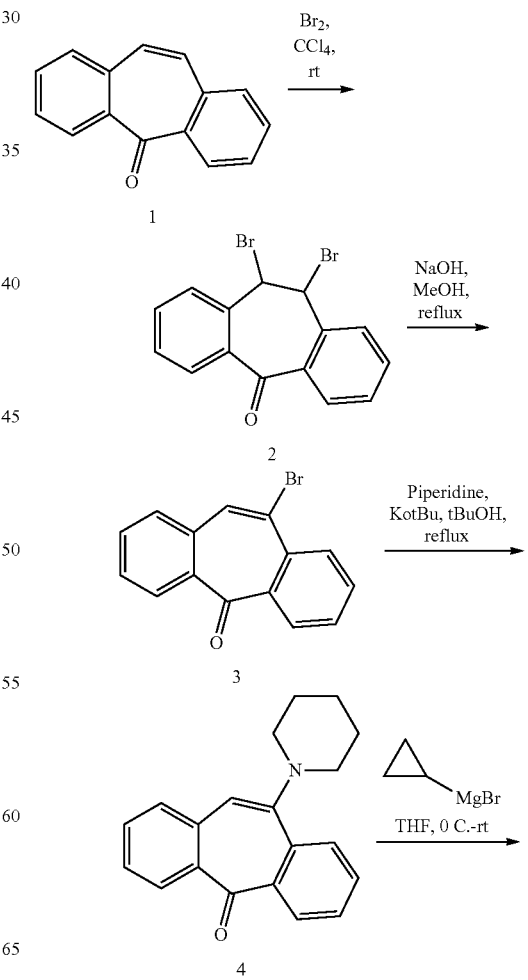

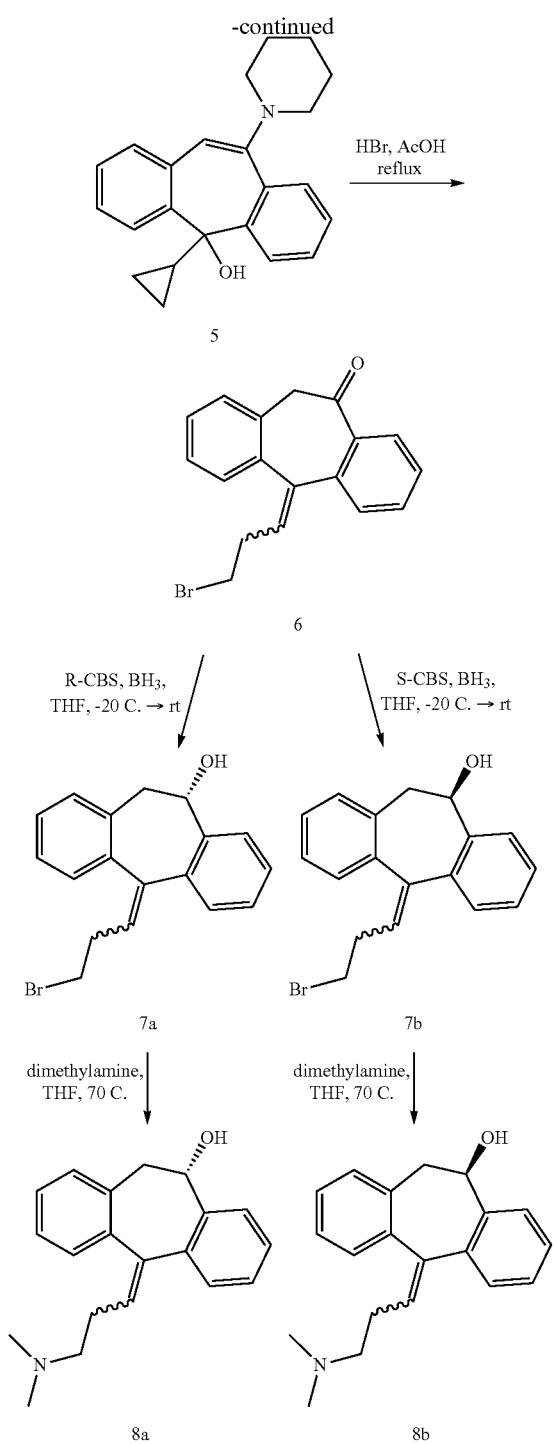

with a small amount of carbon tetrachloride and dried under vacuum to afford 168 g (95%) of 10,11-dibromo-10,11-dihydro-dibenzo[a,d]cyclohepten-5-one (2). ESI MS m/z 366.4, 368.4, 370.5 (M+H)+. $^1$H NMR (d$_6$-DMSO, 250 MHz): 7.97 (2H, d), 7.69-7.64 (4H, m), 7.59-7.53 (2H, m), 6.34 (2H, s).

Preparation of 10-Bromo-dibenzo[a,d]cyclohepten-5-one (3)

Sodium hydroxide (51.5 g, 1.29 mmol) was added to a stirring slurry of 10,11-dibromo-10,11-dihydro-dibenzo[a,d]cyclohepten-5-one (2) (157.0 g, 428.9 mmol) in 1.8 L of methanol and the resulting mixture was heated to 70° C. under nitrogen. LC/MS analysis after six hours revealed consumption of the starting material. The slurry was allowed to cool to room temperature and the solid was collected by vacuum filtration, washed with a small amount of methanol, and dried under vacuum to afford 113 g (92%) of 10-bromo-dibenzo[a,d]cyclohepten-5-one (3). ESI MS m/z 286.5, 288.5 (M+H)+. $^1$H NMR (d$_6$-DMSO, 250 MHz): 8.05 (1H, d), 7.89-7.63 (6H, m), 7.42 (1H, m), 6.67 (1H, s).

Preparation of 10-Piperidin-1-yl-dibenzo[a,d]cyclohepten-5-one (4)

A slurry of 10-bromo-dibenzo[a,d]cyclohepten-5-one (3) (113 g, 396.3 mmol) in 1600 mL t-butanol was prepared, to which was added piperidine (78.3 mL, 792.6 mmol) followed by potassium t-butoxide (62.3 g, 554.8 mmol). The mixture was heated to 85° C. under nitrogen for 5 hours and then was allowed to stir overnight at room temperature. The solvent and volatiles were removed under vacuum, and the resulting semi-solid was dissolved in ethyl acetate (500 mL) and extracted in a separatory funnel with water (200 mL). The aqueous phase was discarded and the organic phase was washed with brine (200 mL). The aqueous phase was discarded and the organic phase concentrated under vacuum to obtain a yellow oil. Trituration with methanol (400 mL) resulted in the formation of a thick white precipitate that was collected by vacuum filtration and dried under vacuum to yield 80 g (75%) of 10-piperidin-1-yl-dibenzo[a,d]cyclohepten-5-one (4). ESI MS m/z 290.2 (M+H)+. $^1$H NMR (d$_6$-DMSO, 250 MHz): 8.01 (1H, d), 7.81-7.67 (6H, m), 7.35 (1H, m), 6.58 (1H, s), 2.89 (4H, m), 1.80-1.60 (6H, m).

Preparation of 5-Cyclopropyl-10-piperidin-1-yl-5H-dibenzo[a,d]cyclohepten-5-ol (5)

10-Piperidin-1-yl-dibenzo[a,d]cyclohepten-5-one (4) (20 g, 69.2 mmol) was dissolved in 60 mL dry tetrahydrofuran and cooled in an ice water bath. A solution of cyclopropylmagnesium bromide (124 mmol, 1.79 equiv.) in tetrahydrofuran (150 mL) was added over a 1 hour period to the cooled reaction mixture. LC/MS analysis fifteen minutes after addition revealed reaction was complete. The reaction was quenched with 200 mL of water and the tetrahydrofuran was removed under vacuum. The resulting pale yellow slurry was stirred overnight and the solid was collected by vacuum filtration and dried under vacuum. The crude 5-cyclopropyl-10-piperidin-1-yl-5H-dibenzo[a,d]cyclohepten-5-ol (5) (69 mmol) was used without further purification in the next step. ESI MS m/z 332.0 (M+H)+.

Preparation of 5-(3-Bromo-propylidene)-5,11-dihydro-dibenzo[a,d]cyclohepten-10-one (6)

5-Cyclopropyl-10-piperidin-1-yl-5H-dibenzo[a,d]cyclohepten-5-ol (5) (69 mmol, 1.00 equiv.) was dissolved in 100

Preparation of 10,11-Dibromo-10,11-dihydro-dibenzo[a,d]cyclohepten-5-one (2)

A solution of bromine (35 mL, 681.1 mmol) in 200 mL carbon tetrachloride was prepared and the resulting solution was added over a 15 minute period to a stirring slurry of dibenzosuberenone (1) (100 g, 484.9 mmol) in 600 mL carbon tetrachloride. LC/MS analysis after five hours showed complete consumption of the starting material. The reaction mixture was filtered and the resulting precipitate was washed mL acetic acid, then 48% aqueous HBr (100 mL) was added and the resulting mixture was heated in a 100° C. oil bath. LC/MS analysis after 18 hours showed that the starting material was consumed. The mixture was diluted with $H_2O$ (100 mL) then extracted in a separatory funnel with ethyl ether (3×100 mL). The aqueous phase was discarded, after which the combined organic phases were washed with saturated sodium bicarbonate (3×50 mL). The aqueous phase was discarded, and the organic phase was filtered through a silica gel plug and concentrated under vacuum to obtain a thick brown oil, which was dissolved in acetonitrile (200 mL) and dried under vacuum. The residue was then dissolved in toluene (200 mL) and again dried under vacuum. The resulting crude 5-(3-bromo-propylidene)-5,11-dihydro-dibenzo[a,d]cyclohepten-10-one (6) was used without further purification in the next step. ESI MS m/z 327.0 $(M+H)^+$. $^1H$ NMR ($d_6$-DMSO, 250 MHz): 7.98 (1H, d), 7.67-7.25 (7H, m), 5.76 (1H, t), 4.46 (1H, d), 3.73 (1H, d), 3.64 (2H, m), 2.83-2.50 (2H, m).

Preparation of (S)-5-(3-Bromo-propylidene)-10,11-dihydro-5H-dibenzo[a,d]cyclohepten-10-ol (7a)

In a dry 40 mL vial with a septum cap, R-CBS catalyst, 1 M in toluene (3.98 mL, 3.98 mmol), 2.0 M borane-dimethyl sulfide in tetrahydrofuran (1.69 mL, 3.37 mmol), and 10 mL dry tetrahydrofuran were premixed. The premix was cooled to −20° C. in an acetonitrile/dry ice bath. A tetrahydrofuran solution of 5-(3-bromo-propylidene)-5,11-dihydro-dibenzo[a,d]cyclohepten-10-one (6) (1.00 g, 3.06 mmol) which had been stored over molecular sieves was then added dropwise. The reaction was allowed to slowly come to room temperature over ~90 minutes. When complete, the reaction was cooled to 0° C. and 1 mL methanol added to quench the reaction. After 15 minutes of further stirring, 1 mL saturated sodium bicarbonate was added. The reaction mixture was then concentrated under reduced pressure and the residue separated between water (50 mL) and dichloromethane (50 mL). The organic layer was then separated, evaporated, and the crude residue was purified by silica gel chromatography using a 5-25% hexanes:ethyl acetate gradient. 0.90 g (89%) (S)-5-(3-Bromo-propylidene)-10,11-dihydro-5H-dibenzo[a,d]cyclohepten-10-ol (7a) was obtained as a faintly yellow oil. ESI MS m/z 623.3 $(2(M-H_2O)+H)^+$.

Preparation of (R)-5-(3-Bromo-propylidene)-10,11-dihydro-5H-dibenzo[a,d]cyclohepten-10-ol (7b)

In a dry 40 mL vial with a septum cap, S-CBS catalyst, 1 M in toluene (3.98 mL, 3.98 mmol), 2.0 M borane-dimethyl sulfide in tetrahydrofuran (1.69 mL, 3.37 mmol), and 10 mL dry tetrahydrofuran were premixed. The premix was cooled to −20° C. in an acetonitrile/dry ice bath. A tetrahydrofuran solution of 5-(3-Bromo-propylidene)-5,11-dihydro-dibenzo[a,d]cyclohepten-10-one (6) (1.00 g, 3.06 mmol) which had been stored over molecular sieves was then added dropwise. The reaction was allowed to slowly come to room temperature over ~90 minutes. When complete, the reaction was cooled to 0° C. and 1 mL methanol added to quench the reaction. After 15 minutes of further stirring, 1 mL saturated sodium bicarbonate was added. The reaction mixture was then evaporated and the residue is separated between water (50 mL) and dichloromethane (50 mL). The organic layer was then separated, evaporated, and the crude residue was purified by silica gel chromatography using a 5-25% hexanes:ethyl acetate gradient. 0.86 g (85%) (S)-5-(3-bromo-propylidene)-10,11-dihydro-5H-dibenzo[a,d]cyclohepten-10-ol (7b) was obtained as a faintly yellow oil. ESI MS m/z 623.3 $(2(M-$ $H_2O)+H)^+$. $^1H$ NMR ($CDCl_3$, 250 MHz): 7.48 (1H, d), 7.33-7.12 (7H, m), 5.91 (1H, t), 5.12-4.70 (1H, 2×m), 3.65 (1H, d), 3.44 (1H, t) 3.06 (1H, dd), 2.73 (2H, m), 1.61 (2H, m).

Preparation of (S)-5-(3-Dimethylamino-propylidene)-10,11-dihydro-5H-dibenzo[a,d]cyclohept-E-en-10-ol trifluoroacetate salt (8a-E) and (S)-5-(3-Dimethylamino-propylidene)-10,11-dihydro-5H-dibenzo[a,d]cyclohept-Z-en-10-ol trifluoroacetate salt (8a-Z)

In a pressure tube, (S)-5-(3-bromo-propylidene)-10,11-dihydro-5H-dibenzo[a,d]cyclohepten-10-ol (7a) (0.90 g, 2.7 mol) was dissolved in 20 mL 2.0 M diethylamine in tetrahydrofuran solution. The tube was sealed and heated to 70° C. for 16 hours. The reaction was cooled to room temperature and the solvent evaporated. The resulting residue was purified by HPLC chromatography to yield 672 mg (61%) of (S)-5-(3-dimethylamino-propylidene)-10,11-dihydro-5H-dibenzo[a,d]cyclohept-E-en-10-ol (8a-E) trifluoroacetate salt as a clear glass solid and 112 mg of (S)-5-(3-dimethylamino-propylidene)-10,11-dihydro-5H-dibenzo[a,d]cyclohept-Z-en-10-ol (8a-Z) trifluoroacetate salt ESI MS m/z 294.4 $(M+H)^+$. (S)-5-(3-Dimethylamino-propylidene)-10,11-dihydro-5H-dibenzo[a,d]cyclohept-E-en-10-ol free base (8a-E): $^1H$ NMR ($d_6$-DMSO, 250 MHz): 8.10 (1H, d), 7.76 (1H, m), 7.51-7.15 (6H, m), 6.22 (1H, t), 4.42 (1H, dd), 3.78 (1H, t), 2.57-2.27 (5H, m), 2.12 (6H, s). (S)-5-(3-Dimethylamino-propylidene)-10,11-dihydro-5H-dibenzo[a,d]cyclohept-Z-en-10-ol trifluoroacetate salt (8a-Z): $^1H$ NMR ($CDCl_3$, 500 MHz): 7.67 (0.5H, d), 7.40-7.04 (7.5H, m), 5.80-5.73 (1H, m), 5.37 (0.5H, dd), 5.07 (0.5H, dd), 3.67-2.45 (13H, m).

The enantiopurity of the E-isomer (8a-E) was determined by analysis on a chiral column: Chiral LC Analysis: 97.9% chiral purity, Chromtech Chiral-AGP 150×4.0 mm, 5μ. Flow: 0.8 mL/min. Mobile Phase: 80% 20 mM sodium phosphate pH 6.0, 20% IPA. Detector: UV at 240 nm. Peak Retention Time: Peak 1 [(S)-E-10-OH]=6.2 min. Peak 2 [(R)-E-10-OH]=11.3 min.

The enantiopurity of the Z-isomer (8a-Z) could not be directly determined as the (R) and (S) enantiomers did not separate sufficiently. The Z-isomer was determined to be of a similar enantiopurity to the E-isomer by reacting the starting material ((S)-5-(3-bromo-propylidene)-10,11-dihydro-5H-dibenzo[a,d]cyclohepten-10-ol) (7a) with butoxypropylamine which enabled analysis of the enantiomers for the Z-isomer due to sufficient separation of the enantiomers using similar chiral HPLC conditions to those described for the E isomer.

Preparation of (R)-5-(3-dimethylamino-propylidene)-10,11-dihydro-5H-dibenzo[a,d]cyclohept-E-en-10-ol trifluoroacetate salt (8b-E) and (R)-5-(3-dimethylamino-propylidene)-10,11-dihydro-5H-dibenzo[a,d]cyclohept-Z-en-10-ol trifluoroacetate salt (8b-Z)

In a pressure tube, (R)-5-(3-bromo-propylidene)-10,11-dihydro-5H-dibenzo[a,d]cyclohepten-10-ol (7b) (0.86 g, 2.6 mol) was dissolved in 20 mL 2.0 M diethylamine in tetrahydrofuran solution. The tube was sealed and heated to 70° C. for 16 hours. The reaction was cooled to room temperature and the solvent evaporated. The resulting residue was purified by HPLC chromatography to yield 635 mg (60%) of (R)-5-(3-dimethylamino-propylidene)-10,11-dihydro-5H-dibenzo[a,d]cyclohept-E-en-10-ol trifluoroacetate salt (8b-E) as a clear glass solid and 124 mg of (R)-5-(3-dimethylaminopropylidene)-10,11-dihydro-5H-dibenzo[a,d]cyclohept-Z-en-10-ol TFA salt (8b-Z) as a clear glass solid. ESI MS m/z 294.4 (M+H)$^+$. (R)-5-(3-Dimethylamino-propylidene)-10,11-dihydro-5H-dibenzo[a,d]cyclohept-Z-en-10-ol trifluoroacetate salt (8b-Z): $^1$H NMR (CDCl$_3$, 500 MHz): 7.67 (0.5H, d), 7.40-7.04 (7.5H, m), 5.80-5.73 (1H, m), 5.37 (0.5H, dd), 5.07 (0.5H, dd), 3.66-2.42 (13H, m).

The enantiopurity of the E-isomer (8b-E) was determined by analysis on a chiral column: Chiral LC Analysis: 96.1% chiral purity, Chromtech Chiral-AGP 150×4.0 mm, 5μ. Flow: 0.8 mL/min. Mobile Phase: 80% 20 mM sodium phosphate pH 6.0, 20% IPA. Detector: UV at 240 nm. Peak Retention Time: Peak 1 [(S)-E-10-OH]=6.5 min. Peak 2 [(R)-E-10-OH]=9.5 min.

The enantiopurity of the Z-isomer (8b-Z) could not be directly determined as the (R) and (S) enantiomers did not separate sufficiently. The Z-isomer was determined to be of a similar enantiopurity to the E-isomer by reacting the starting material ((R)-5-(3-bromo-propylidene)-10,11-dihydro-5H-dibenzo[a,d]cyclohepten-10-ol) (7b) with butoxypropylamine which enabled analysis of the enantiomers for the Z-isomer due to sufficient separation of the enantiomers using similar chiral HPLC conditions to those described for the E isomer.

EXAMPLE 2

Preparation of (R)-5-(3-dimethylamino-propylidene)-10-OmPEG$_4$-10,11-dihydro-5H-dibenzo[a,d]cyclohept-E-ene trifluoroacetate salt

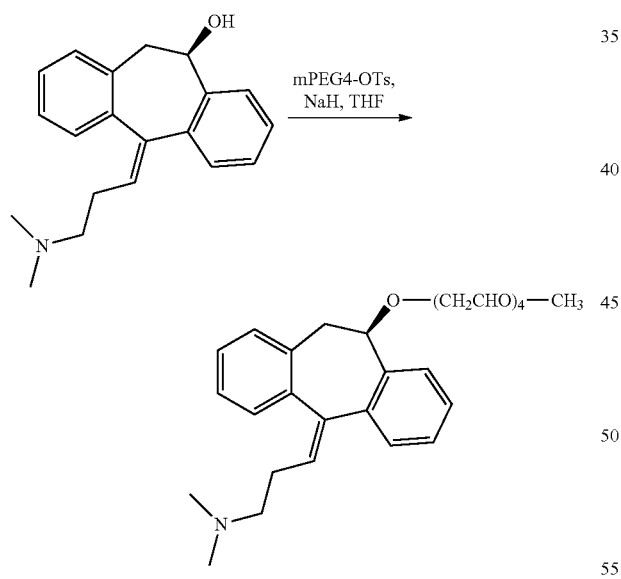

In a 8 mL vial, (R)-5-(3-dimethylamino-propylidene)-10,11-dihydro-5H-dibenzo[a,d]cyclohept-E-en-10-ol (8b-E) (150 mg, 0.52 mmol) was dissolved in 3 mL tetrahydrofuran. To the stirring solution was added sodium hydride (60% dispersion in oil) (25 mg, 0.61 mmol). After 30 minutes, mPEG4-OTs (223 mg, 0.61 mmol) was added and the reaction was heated to 60° C. for 16 hours. The reaction was quenched with methanol (1 mL) and ethyl acetate (20 mL) and water (20 mL) were added. The aqueous layer was extracted with ethyl acetate (3×30 mL). The combined organics were washed with brine (50 mL), dried over sodium sulfate, filtered, and concentrated under reduced pressure. The resulting residue was purified by HPLC chromatography to yield 87 mg of (R)-5-(3-dimethylamino-propylidene)-10-OmPEG$_4$-10,11-dihydro-5H-dibenzo[a,d]cyclohept-E-ene trifluoroacetate salt as a clear yellow oil. ESI MS m/z 484.3 (M+H)$^+$.

EXAMPLE 3

(R)-5-(3-dimethylamino-propylidene)-10-OmPEG$_1$-10,11-dihydro-5H-dibenzo[a,d]cyclohept-E-ene trifluoroacetate salt (R)-5-(3-dimethylamino-propylidene)-10-OmPEG$_1$-10,11-dihydro-5H-dibenzo[a,d]cyclohept-E-ene trifluoroacetate salt was prepared from (R)-5-(3-dimethylamino-propylidene)-10,11-dihydro-5H-dibenzo[a,d]cyclohept-E-en-10-ol (8b-E), sodium hydride, and mPEG$_1$-OMs in tetrahydrofuran by following the procedure described in Example 2. ESI MS m/z 352.3 (M+H)$^+$. $^1$H NMR (CDCl$_3$, 500 MHz): 7.48-7.04 (8H, m), 5.81 (0.5H, t), 5.72 (0.5H, t), 4.92-4.86 (0.5H, m), 4.68 (0.5H, dd), 3.81-2.51 (19H, m).

EXAMPLE 4

(R)-5-(3-dimethylamino-propylidene)-10-OmPEG$_2$-10,11-dihydro-5H-dibenzo[a,d]cyclohept-E-ene trifluoroacetate salt (R)-5-(3-dimethylamino-propylidene)-100 mPEG$_2$-10,11-dihydro-5H-dibenzo[a,d]cyclohept-E-ene trifluoroacetate salt was prepared from (R)-5-(3-dimethylamino-propylidene)-10,11-dihydro-5H-dibenzo[a,d]cyclohept-E-en-10-ol (8b-E), sodium hydride, and mPEG$_2$-OMs in tetrahydrofuran by following the procedure described in Example 2. ESI MS m/z 396.4 (M+H)$^+$. $^1$H NMR (CDCl$_3$, 500 MHz): 7.48-7.04 (8H, m), 5.83 (0.5H, t), 5.73 (0.5H, t), 4.90-4.85 (0.5H, m), 4.70-4.65 (0.5H, m), 3.85-2.57 (23H, m).

EXAMPLE 5

(R)-5-(3-dimethylamino-propylidene)-10-OmPEG$_6$-10,11-dihydro-5H-dibenzo[a,d]cyclohept-E-ene trifluoroacetate salt (R)-5-(3-dimethylamino-propylidene)-10-OmPEG$_6$-10,11-dihydro-5H-dibenzo[a,d]cyclohept-E-ene trifluoroacetate salt was prepared from (R)-5-(3-dimethylamino-propylidene)-10,11-dihydro-5H-dibenzo[a,d]cyclohept-E-en-10-ol (8b-E), sodium hydride, and mPEG$_6$-OTs in tetrahydrofuran by following the procedure described in Example 2. ESI MS m/z 572.5 (M+H)$^+$.

EXAMPLE 6

(R)-5-(3-dimethylamino-propylidene)-10-OmPEG$_8$-10,11-dihydro-5H-dibenzo[a,d]cyclohept-E-ene trifluoroacetate salt (R)-5-(3-dimethylamino-propylidene)-10-OmPEG$_8$-10,11-dihydro-5H-dibenzo[a,d]cyclohept-E-ene trifluoroacetate salt was prepared from (R)-5-(3-dimethylamino-propylidene)-10,11-dihydro-5H-dibenzo[a,d]cyclohept-E-en-10-ol (8b-E), sodium hydride, and mPEG$_8$-OMs in tetrahydrofuran by following the procedure described in Example 2. ESI MS m/z 660.4 (M+H)$^+$.

EXAMPLE 7

(S)-5-(3-dimethylamino-propylidene)-10-OmPEG$_4$-10,11-dihydro-5H-dibenzo[a,d]cyclohept-E-ene trifluoroacetate salt (S)-5-(3-dimethylamino-propylidene)-10-OmPEG$_4$-10,11-dihydro-5H-dibenzo[a,d]cyclohept-E-ene trifluoroacetate salt was prepared from (S)-5-(3-dimethylamino-propylidene)-10,11-dihydro-5H-dibenzo[a,d]cyclohept-E-en-10-ol (8a-E), sodium hydride, and mPEG$_4$-OTs in tetrahydrofuran by following the procedure described in Example 2. ESI MS m/z 484.3 (M+H)$^+$.

EXAMPLE 8

(S)-5-(3-dimethylamino-propylidene)-10-OmPEG$_6$-10,11-dihydro-5H-dibenzo[a,d]cyclohept-E-ene trifluoroacetate salt (S)-5-(3-dimethylamino-propylidene)-10-OmPEG$_6$-10,11-dihydro-5H-dibenzo[a,d]cyclohept-E-ene trifluoroacetate salt was prepared from (S)-5-(3-dimethylamino-propylidene)-10,11-dihydro-5H-dibenzo[a,d]cyclohept-E-en-10-ol (8a-E), sodium hydride, and mPEG$_6$-OTs in tetrahydrofuran by following the procedure described in Example 2. ESI MS m/z 572.5 (M+H)$^+$.

EXAMPLE 9

(S)-5-(3-dimethylamino-propylidene)-10-OmPEG$_8$-10,11-dihydro-5H-dibenzo[a,d]cyclohept-E-ene trifluoroacetate salt (S)-5-(3-dimethylamino-propylidene)-10-OmPEG$_8$-10,11-dihydro-5H-dibenzo[a,d]cyclohept-E-ene trifluoroacetate salt was prepared from (S)-5-(3-dimethylamino-propylidene)-10,11-dihydro-5H-dibenzo[a,d]cyclohept-E-en-10-ol (8a-E), sodium hydride, and mPEG$_8$-OMs in tetrahydrofuran by following the procedure described in Example 2. ESI MS m/z 660.7 (M+H)$^+$.

EXAMPLE 10

(R)-5-(3-dimethylamino-propylidene)-10-OmPEG$_4$-10,11-dihydro-5H-dibenzo[a,d]cyclohept-Z-ene trifluoroacetate salt (R)-5-(3-dimethylamino-propylidene)-10-OmPEG$_4$-10,11-dihydro-5H-dibenzo[a,d]cyclohept-Z-ene trifluoroacetate salt was prepared from (R)-5-(3-dimethylamino-propylidene)-10,11-dihydro-5H-dibenzo[a,d]cyclohept-Z-en-10-ol (8b-Z), sodium hydride, and mPEG$_4$-OTs in tetrahydrofuran by following the procedure described in Example 2. ESI MS m/z 484.6 (M+H)$^+$. $^1$H NMR (CDCl$_3$, 500 MHz): 7.58 (0.67H, d), 7.50-7.02 (7.33H, m), 5.84 (0.67H, t), 5.65 (0.33H, dd), 4.99 (0.67H, dd), 4.70-4.65 (0.33H, m), 3.86-2.56 (31H, m).

EXAMPLE 11

(R)-5-(3-dimethylamino-propylidene)-10-OmPEG$_6$-10,11-dihydro-5H-dibenzo[a,d]cyclohept-Z-ene trifluoroacetate salt (R)-5-(3-dimethylamino-propylidene)-10-OmPEG$_6$-10,11-dihydro-5H-dibenzo[a,d]cyclohept-Z-ene trifluoroacetate salt was prepared from (R)-5-(3-dimethylamino-propylidene)-10,11-dihydro-5H-dibenzo[a,d]cyclohept-Z-en-10-ol (8b-Z), sodium hydride, and mPEG$_6$-OTs in tetrahydrofuran by following the procedure described in Example 2. ESI MS m/z 572.5 (M+H)$^+$. $^1$H NMR (CDCl$_3$, 500 MHz): 7.59 (0.67H, d), 7.40-7.02 (7.33H, m), 5.84 (0.67H, t), 5.65 (0.33H, t), 4.99 (0.67H, dd), 4.70-4.65 (0.33H, m), 3.86-2.55 (39H, m).

EXAMPLE 12

(R)-5-(3-dimethylamino-propylidene)-10-OmPEG$_8$-10,11-dihydro-5H-dibenzo[a,d]cyclohept-Z-ene trifluoroacetate salt (R)-5-(3-dimethylamino-propylidene)-10-OmPEG$_8$-10,11-dihydro-5H-dibenzo[a,d]cyclohept-Z-ene trifluoroacetate salt was prepared from (R)-5-(3-dimethylamino-propylidene)-10,11-dihydro-5H-dibenzo[a,d]cyclohept-Z-en-10-ol (8b-Z), sodium hydride, and mPEG$_8$-OMs in tetrahydrofuran by following the procedure described in Example 2. ESI MS m/z 660.7 (M+H)$^+$. $^1$H NMR (CDCl$_3$, 500 MHz): 7.59 (0.67H, d), 7.40-7.02 (7.33H, m), 5.84 (0.67H, t), 5.68-5.63 (0.33H, m), 4.99 (0.67H, dd), 4.70-4.65 (0.33H, m), 3.86-2.54 (47H, m).

EXAMPLE 13

(S)-5-(3-dimethylamino-propylidene)-10-OmPEG$_4$-10,11-dihydro-5H-dibenzo[a,d]cyclohept-Z-ene trifluoroacetate salt (S)-5-(3-dimethylamino-propylidene)-10-OmPEG$_4$-10,11-dihydro-5H-dibenzo[a,d]cyclohept-Z-ene trifluoroacetate salt was prepared from (S)-5-(3-dimethylamino-propylidene)-10,11-dihydro-5H-dibenzo[a,d]cyclohept-Z-en-10-ol (8b-Z), sodium hydride, and mPEG$_4$-OTs in tetrahydrofuran by following the procedure described in Example 2. ESI MS m/z 484.6 (M+H)$^+$. $^1$H NMR (CDCl$_3$, 500 MHz): 7.58 (0.67H, d), 7.38-7.02 (7.33H, m), 5.84 (0.67H, t), 5.72-5.68 (0.33H, m), 5.00 (0.67H, dd), 4.73-4.69 (0.33H, m), 3.86-2.56 (31H, m).

EXAMPLE 14

(S)-5-(3-dimethylamino-propylidene)-10-OmPEG$_6$-10,11-dihydro-5H-dibenzo[a,d]cyclohept-Z-ene trifluoroacetate salt (S)-5-(3-dimethylamino-propylidene)-10-OmPEG$_6$-10,11-dihydro-5H-dibenzo[a,d]cyclohept-Z-ene trifluoroacetate salt was prepared from (S)-5-(3-dimethylamino-propylidene)-10,11-dihydro-5H-dibenzo[a,d]cyclohept-Z-en-10-ol (8a-Z), sodium hydride, and mPEG$_6$-OTs in tetrahydrofuran by following the procedure described in Example 2. ESI MS m/z 572.5 (M+H)$^+$. $^1$H NMR (CDCl$_3$, 500 MHz): 7.58 (0.67H, d), 7.39-7.02 (7.33H, m), 5.84 (0.67H, t), 5.72-5.67 (0.33H, m), 4.99 (0.67H, dd), 4.72-4.68 (0.33H, m), 3.85-2.56 (39H, m).

EXAMPLE 15

(S)-5-(3-dimethylamino-propylidene)-10-OmPEG$_8$-10,11-dihydro-5H-dibenzo[a,d]cyclohept-Z-ene trifluoroacetate salt (S)-5-(3-dimethylamino-propylidene)-10-OmPEG$_8$-10,11-dihydro-5H-dibenzo[a,d]cyclohept-Z-ene trifluoroacetate salt was prepared from (S)-5-(3-dimethylamino-propylidene)-10,11-dihydro-5H-dibenzo[a,d]cyclohept-Z-en-10-ol (8a-Z) sodium hydride, and mPEG$_8$-OMs in tetrahydrofuran by following the procedure described in Example 2. ESI MS m/z 660.7 (M+H)$^+$. $^1$H NMR (CDCl$_3$, 500 MHz): 7.58 (0.67H, d), 7.40-7.02 (7.33H, m), 5.84 (0.67H, t), 5.65 (0.33H, t), 4.99 (0.67H, dd), 4.70-4.66 (0.33H, m), 3.86-2.54 (47H, m).

EXAMPLE 16

Preparation of 5-(3-Dimethylamino-propylidene)-10,11-dihydro-5H-dibenzo[a,d]cyclohept-E-en-2-OmPEG$_4$ hydrochloride salt and 5-(3-Dimethylamino-propylidene)-10,11-dihydro-5H-dibenzo[a,d]cyclohept-Z-en-2-OmPEG$_4$ hydrochloride salt 5-(3-Dimethylamino-propylidene)-10,11-dihydro-5H-dibenzo[a,d]cyclohept-E-en-2-OmPEG$_4$ hydrochloride salt and 5-(3-Dimethylamino-propylidene)-10,11-dihydro-5H-dibenzo[a,d]cyclohept-Z-en-2-OmPEG$_4$ hydrochloride salt were prepared using the general reaction scheme provided below, where mPEG$_x$ represents a methyl capped ethylene glycol group where x is an integer representing the number of ethylene glycol subunits in each PEG group. In the example below, x is 4.

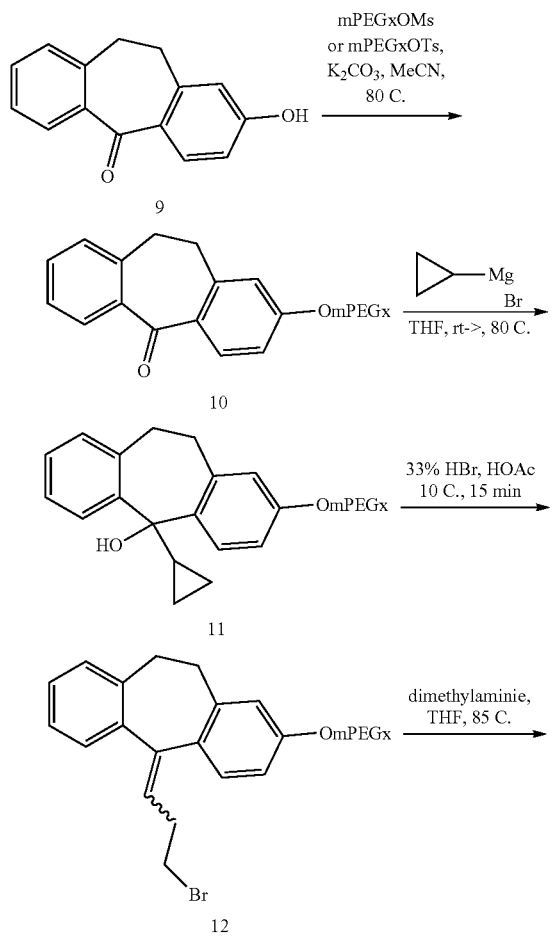

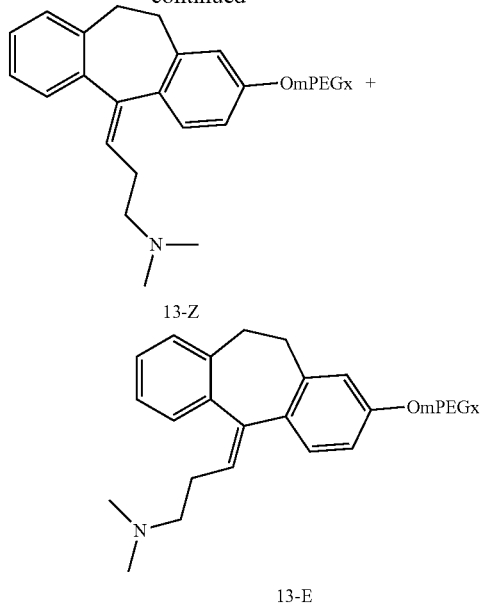

Preparation of 2-OmPEG$_4$-10,11-dihydro-dibenzo[a,d]cyclohepten-5-one (10)

To a stirred solution of 2-hydroxy-5-dibenzosuberone (9) (1.0 g, 4.5 mmol) in acetonitrile (20 mL) was added potassium carbonate (1.2 g, 9.0 mmol) and mPEG$_4$-OMs (1.9 g, 6.7 mmol). The resulting mixture was heated at 80° C. with stirring for 16 h, cooled to room temperature, and then concentrated under reduced pressure to dryness. The solid residue was treated with water (20 mL) and ethyl acetate (100 mL). After the ethyl acetate layer was separated, the aqueous layer was extracted with ethyl acetate (50 mL×2). The combined ethyl acetate extracts were washed with brine, dried over magnesium sulfate, filtered, and evaporated to afford 2-OmPEG$_4$-10,11-dihydro-dibenzo[a,d]cyclohepten-5-one (10) (1.7 g, 92%) as an off-white viscous oil. ESI MS m/z 415.1 (M+H)$^+$. This material was used in the next step without further purification.

Preparation of 5-Cyclopropyl-2-OmPEG$_4$-10,11-dihydro-5H-dibenzo[a,d]cyclohepten-5-ol (11)

A solution of 2-OmPEG$_4$-10,11-dihydro-dibenzo[a,d]cyclohepten-5-one (10) (1.1 g, 2.6 mmol) in anhydrous tetrahydrofuran (10 mL) was cooled to 10° C. and a 0.5 M solution of cyclopropylmagnesium bromide in tetrahydrofuran (15 mL, 7.5 mmol) was added with stirring under nitrogen for 10 min. After stirring at room temperature for an additional 10 min, the reaction mixture was heated at 80° C. for 3 h. The reaction mixture was quenched with saturated ammonium chloride at room temperature and then extracted with ethyl acetate (30 mL×3). The combined ethyl acetate extracts were washed with brine, dried over magnesium sulfate, filtered, and evaporated to afford cyclopropyl-2-OmPEG$_4$-10,11-dihydro-5H-dibenzo[a,d]cyclohepten-5-ol (11) (1.2 g, 100%) as a yellow viscous oil. ESI MS m/z 439.2 (M–H2O+H)$^+$. This material was used in the next step without further purification.

Preparation of 5-(3-Bromo-propylidene)-2-OmPEG$_4$-10,11-dihydro-5H-dibenzo[a,d]cycloheptene (12)

A solution of 5-cyclopropyl-2-OmPEG4-10,11-dihydro-5H-dibenzo[a,d]cyclohepten-5-ol (11) (1.2 g, 2.9 mmol) in glacial acetic acid (4 mL) was cooled to 0° C. A solution of 33% hydrogen bromide in acetic acid (2 mL) was added with stirring and the reaction mixture was stirred at 10° C. for 15 min. The mixture was poured into saturated sodium bicarbonate and basified with solid sodium bicarbonate to pH ~8-9. The resulting mixture was extracted with ethyl acetate (30 mL×3). The combined extracts were washed with brine, dried over magnesium sulfate, filtered, and evaporated to afford the 5-(3-bromo-propylidene)-2-OmPEG4-10,11-dihydro-5H-dibenzo[a,d]cycloheptene (12) (1.4 g, 100%) as a brown viscous oil. ESI MS m/z 519.2 (M+H)$^+$.

Preparation of 5-(3-Dimethylamino-propylidene)-10,11-dihydro-5H-dibenzo[a,d]cyclohept-E-en-2-OmPEG$_4$ hydrochloride salt (13-E) and 5-(3-Dimethylamino-propylidene)-10,11-dihydro-5H-dibenzo[a,d]cyclohept-Z-en-2-OmPEG$_4$ hydrochloride salt (13-Z). A solution of 5-(3-bromo-propylidene)-2-OmPEG$_4$-10,11-dihydro-5H-dibenzo[a,d]cycloheptene (12) (1.5 g, 2.9 mmol) in tetrahydrofuran (10 mL) was mixed with a 2M solution of dimethylamine in tetrahydrofuran (10 mL) at room temperature. The resulting mixture was sealed in a microwave tube and heated at 85° C. for 16 h, then at 110° C. for 2 h. The reaction mixture was cooled down to room temperature and then evaporated to dryness. The viscous oily residue was checked by LCMS (mixture of E,Z isomers in a ratio of 3:2) and purified by HPLC to afford the 5-(3-dimethylamino-propylidene)-10,11-dihydro-5H-dibenzo[a,d]cyclohept-E-en-2-OmPEG$_4$ trifluoroacetic acid salt (13-E) and 5-(3-dimethylamino-propylidene)-10,11-dihydro-5H-dibenzo[a,d]cyclohept-Z-en-2-OmPEG$_4$ trifluoroacetic acid salt (13-Z) separately. ESI MS m/z 484.4 (M+H)$^+$.

The 5-(3-dimethylamino-propylidene)-10,11-dihydro-5H-dibenzo[a,d]cyclohept-E-en-2-OmPEG$_4$ trifluoroacetic acid salt was treated with a 2M solution of HCl in ether and acetonitrile, evaporated, and similarly retreated two more times to provide 5-(3-dimethylamino-propylidene)-10,11-dihydro-5H-dibenzo[a,d]cyclohept-E-en-2-OmPEG$_4$ hydrochloride salt (185 mg). The 5-(3-dimethylamino-propylidene)-10,11-dihydro-5H-dibenzo[a,d]cyclohept-Z-en-2-OmPEG$_4$ trifluoroacetic acid salt was treated similarly to afford the 5-(3-dimethylamino-propylidene)-10,11-dihydro-5H-dibenzo[a,d]cyclohept-Z-en-2-mPEG$_4$ hydrochloride salt (177 mg).

5-(3-Dimethylamino-propylidene)-10,11-dihydro-5H-dibenzo[a,d]cyclohept-E-en-2-OmPEG$_4$ hydrochloride salt: $^1$H NMR (d$_6$-DMSO, 250 MHz): 9.91 (1H, bs), 7.32-7.10 (5H, m), 6.88 (1H, d), 6.77 (1H, dd), 5.75 (1H, t), 4.05 (1H, t), 3.71 (1H, t), 3.56-3.42 (16H, m), 3.28-3.11 (7H, m), 2.83-2.67 (7H, m).

5-(3-Dimethylamino-propylidene)-10,11-dihydro-5H-dibenzo[a,d]cyclohept-Z-en-2-OmPEG$_4$ hydrochloride salt: $^1$H NMR (d$_6$-DMSO, 250 MHz): 9.91 (1H, bs), 7.32-7.03 (5H, m), 6.88 (1H, d), 6.77 (1H, dd), 5.75 (1H, t), 4.08 (1H, t), 3.73 (1H, t), 3.60-3.40 (16H, m), 3.20-3.12 (7H, m) 2.82-2.67 (7H, m).

EXAMPLE 17

Preparation of 5-(3-Dimethylamino-propylidene)-10,11-dihydro-5H-dibenzo[a,d]cyclohept-E-en-2-OmPEG$_6$ hydrochloride salt and 5-(3-Dimethylamino-propylidene)-10,11-dihydro-5H-dibenzo[a,d]cyclohept-Z-en-2-OmPEG$_6$ hydrochloride salt 5-(3-bromo-propylidene)-2-OmPEG$_6$-10,11-dihydro-5H-dibenzo[a,d]cycloheptene was prepared as described in Example 16, where mPEG$_6$-OMs was used in place of mPEG$_4$-OMs. 5-(3-Dimethylamino-propylidene)-10,11-dihydro-5H-dibenzo[a,d]cyclohept-E-en-2-OmPEG$_6$ hydrochloride salt and 5-(3-Dimethylamino-propylidene)-10,11-dihydro-5H-dibenzo[a,d]cyclohept-Z-en-2-OmPEG$_6$ hydrochloride salt were prepared from 5-(3-bromo-propylidene)-2-OmPEG$_6$-10,11-dihydro-5H-dibenzo[a,d]cycloheptene and 2 M solution of dimethylamine in tetrahydrofuran by following the procedure described in Example 16. ESI MS m/z 615.6 (M+H)$^+$.

5-(3-Dimethylamino-propylidene)-10,11-dihydro-5H-dibenzo[a,d]cyclohept-E-en-2-OmPEG$_6$ hydrochloride salt: $^1$H NMR (d$_6$-DMSO, 250 MHz): 9.91 (1H, bs), 7.31-7.08 (5H, m), 6.88 (1H, d), 6.77 (1H, dd,), 5.73 (1H, t), 4.04 (1H, t), 3.72 (1H, t), 3.57-3.39 (24H, m), 3.22-3.11 (7H, m), 2.73-2.5 (7H, m).

5-(3-Dimethylamino-propylidene)-10,11-dihydro-5H-dibenzo[a,d]cyclohept-Z-en-2-OmPEG$_6$ hydrochloride salt: $^1$H NMR (d$_6$-DMSO, 250 MHz): 9.91 (1H, bs), 7.27-7.03 (5H, m), 6.88 (1H, d), 6.77 (1H, dd), 5.75 (1H, t), 4.07 (1H, t), 3.73 (1H, t), 3.60-3.40 (24H, m), 3.20-3.12 (7H, m) 2.78-2.67 (7H, m).

EXAMPLE 18

Preparation of 5-(3-Dimethylamino-propylidene)-10,11-dihydro-5H-dibenzo[a,d]cyclohept-E-en-2-OmPEG$_8$ hydrochloride salt and 5-(3-Dimethylamino-propylidene)-10,11-dihydro-5H-dibenzo[a,d]cyclohept-Z-en-2-OmPEG$_8$ hydrochloride salt 5-(3-bromo-propylidene)-2-OmPEG$_8$-10,11-dihydro-5H-dibenzo[a,d]cycloheptene was prepared as described in Example 16, where mPEG$_8$-OMs was used in place of mPEG$_4$-OMs. 5-(3-Dimethylamino-propylidene)-10,11-dihydro-5H-dibenzo[a,d]cyclohept-E-en-2-OmPEG$_8$ hydrochloride salt and 5-(3-Dimethylamino-propylidene)-10,11-dihydro-5H-dibenzo[a,d]cyclohept-Z-en-2-OmPEG$_8$ hydrochloride salt was prepared from 5-(3-bromo-propylidene)-2-OmPEG$_8$-10,11-dihydro-5H-dibenzo[a,d]cycloheptene and 2 M solution of dimethylamine in tetrahydrofuran by following the procedure described in Example 16. ESI MS m/z 660.5 (M+H)$^+$.

5-(3-Dimethylamino-propylidene)-10,11-dihydro-5H-dibenzo[a,d]cyclohept-E-en-2-OmPEG$_8$ hydrochloride salt: $^1$H NMR (d$_6$-DMSO, 250 MHz): 9.91 (1H, bs), 7.31-7.14 (5H, m), 6.76 (1H, dd), 6.88 (1H, d), 5.73 (1H, t), 4.04 (1H, t), 3.71 (1H, t), 3.54-3.39 (32H, m), 3.22-3.13 (7H, m), 2.73-2.60 (7H, m).

5-(3-Dimethylamino-propylidene)-10,11-dihydro-5H-dibenzo[a,d]cyclohept-Z-en-2-OmPEG8 hydrochloride salt: $^1$H NMR (d$_6$-DMSO, 250 MHz): 9.91 (1H, bs), 7.23-7.03 (5H, m), 6.88 (1H, d), 6.80 (1H, dd), 5.75 (1H, t), 4.07 (1H, t), 3.73 (1H, t), 3.58-3.41 (32H, m), 3.23-3.15 (7H, m) 2.78-2.67 (7H, m).

EXAMPLE 19

Alternative preparation of 5-[3-Dimethylamino-propylidene]-10,11-dihydro-2-OmPEG6-5H-dibenzo[a,d]cycloheptene 5-[3-Dimethylamino-propylidene]-10,11-dihydro-2-OmPEG6-5H-dibenzo[a,d]cycloheptene was prepared using the general reaction scheme provided below, where mPEGx represents a methyl capped ethylene glycol group where x is an integer representing the number of ethylene glycol subunits in each PEG group. In the example below, x is 6.

Preparation of (3-(Dimethylamino)propyl)triphenylphosphonium bromide hydrobromide salt To a suspension of 3-bromopropyltriphenylphosphonium bromide (1.0 g, 2.1 mmol) in ethanol (5 mL) was added a solution of 40% dimethylamine in water (3 mL) at room temperature. The mixture was stirred and heated at 100° C. for 30 min in a sealed microwave tube. After the reaction mixture was concentrated under reduced pressure, the solid residue was recrystallized in acetonitrile to afford (3-(dimethylamino)propyl)triphenylphosphonium bromide hydro-

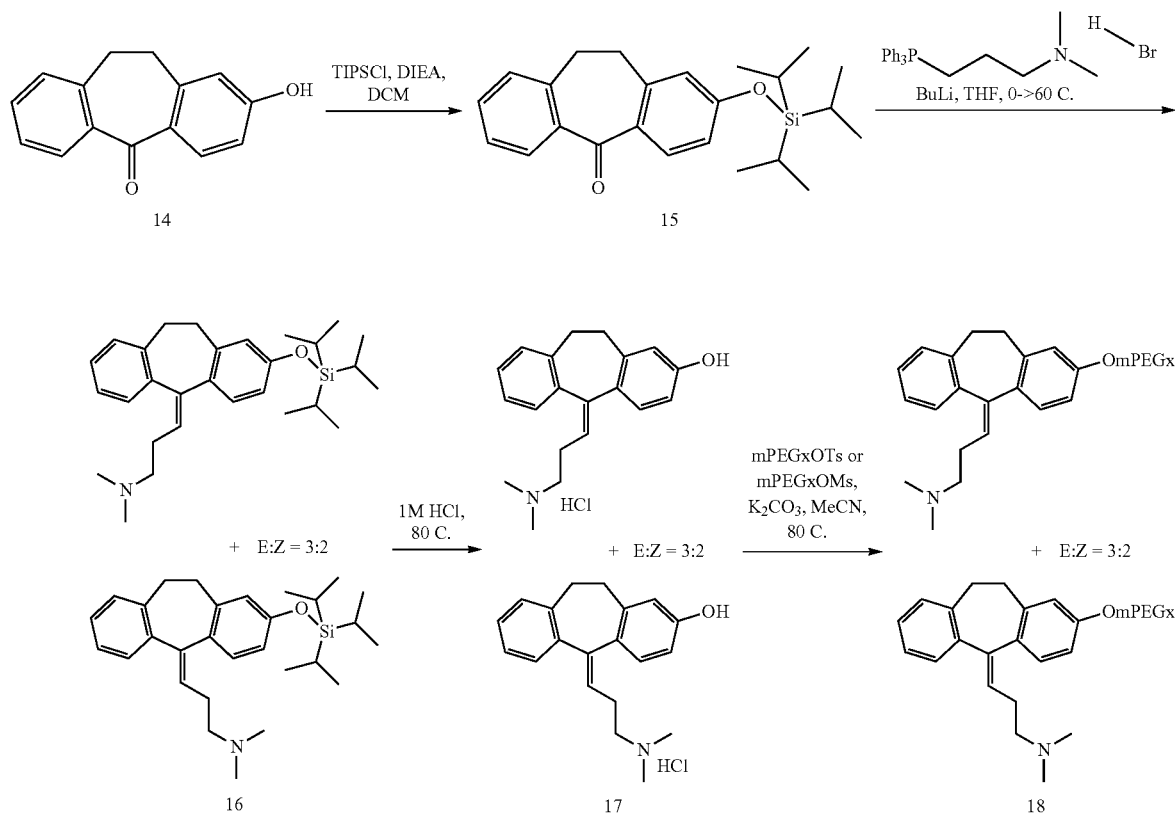

Preparation of 2-Triisopropylsilanyloxy-10,11-dihydro-dibenzo[a,d]cyclohepten-5-one (15)

2-Hydroxydibenzosuberone (14) (2.00 g, 8.93 mmol) was dissolved in dichloromethane (50 mL). To this solution was added triisopropylsilylchloride (1.89 g, 9.82 mmol) and Hunig's base (1.85 mL, 10.71 mmol). The reaction was stirred at room temperature for 5 hours. When the reaction was complete, the organics were washed with 1M potassium carbonate (3×50 mL), 0.5 M citric acid (3×50 mL), brine (50 mL) and dried over magnesium sulfate. The organic solution was then filtered and concentrated under reduced pressure to yield 3.4 g (100%) of 2-triisopropylsilanyloxy-10,11-dihydro-dibenzo[a,d]cyclohepten-5-one (15) as a yellow oil. ESI MS m/z 381.8 (M+H)$^+$. NMR (d$_6$-DMSO, 250 MHz): 7.29-7.22 (5H, m), 7.15-7.07 (2H, m), 3.57 (5H, m), 3.03 (2H, q), 1.41 (18H, d).

bromide salt (0.90 g, 82%) as a white solid, and was used in the following step. ESI MS m/z 348.3 (Ph$_3$PCH$_2$CH$_2$CH$_2$NMe$_2$)$^+$.

Preparation of Dimethyl-{3-[2-triisopropylsilanyloxy-10,11-dihydro-dibenzo[a,d]cyclohepten-(5)-ylidene}-propyl]-amine (16)

2-Triisopropylsilanyloxy-10,11-dihydro-dibenzo[a,d]cyclohepten-5-one (15) (2.00 g, 5.26 mmol) was dissolved in 40 mL dry tetrahydrofuran. In a separate flask, (3-dimethylamino-propyl)-triphenyl-phosphonium bromide hydrobromide salt (2.72 g, 6.32 mmol) was suspended in 40 mL dry tetrahydrofuran and cooled to 5° C. in an ice bath. 2.5 M n-Butyllithium in hexanes (2.94 mL, 7.36 mmol) was added slowly and then the reaction was allowed to stir for 20 minutes. The 2-triisopropylsilanyloxy-10,11-dihydro-dibenzo[a,d]cyclohepten-5-one solution was then added slowly and the reaction heated to 60° C. When the reaction was complete, it was cooled in an ice bath and water was added slowly to quench the reaction. Tetrahydrofuran was then evaporated off and the residue separated between ethyl acetate (100 mL) and water (100 mL). The organic layer was washed with saturated sodium bicarbonate (3×100 mL), brine (50 mL), dried over magnesium sulfate, filtered, and evaporated. The residue was re-dissolved in dichloromethane and run through a silica gel plug to remove remaining triphenylphosphine. The resulting solution was evaporated to yield 1.4 g (58%) of dimethyl-{3-[2-triisopropylsilanyloxy-10,11-dihydro-dibenzo[a,d]cyclohepten-(5)-ylidene]-propyl}-amine (16) as a yellow oil. ESI MS m/z 451.0 (M+H)$^+$.

Preparation of 5-[3-Dimethylamino-propylidene]-10, 11-dihydro-5H-dibenzo[a,d]cyclohepten-2-ol hydrochloride salt (17)

Dimethyl-{3-[2-triisopropylsilanyloxy-10,11-dihydro-dibenzo[a,d]cyclohepten-(5)-ylidene]-propyl}-amine (16) (1.40 g, 3.11 mmol) was dissolved in 10 mL isopropyl alcohol and 20 mL 2.0 M hydrochloric acid. The mixture was heated to 80° C. and stirred for several hours. When complete, the reaction was allowed to cool to room temperature and diluted with water (100 mL). The aqueous layer was washed with diethyl ether (3×100 mL) and then evaporated down to yield 0.8 g (80%) of 5-[3-dimethylamino-propylidene]-10,11-dihydro-5H-dibenzo[a,d]cyclohepten-2-ol hydrochloride salt (17). By HPLC, the product mixture was determined to be 3:2. ESI MS m/z 294.6 (M+H)$^+$. A small amount of the material was purified by HPLC to afford 5-[3-dimethylamino-propylidene]-10,11-dihydro-5H-dibenzo[a,d]cyclohept-E-en-2-ol hydrochloride salt (86 mg) and 5-[3-dimethylamino-propylidene]-10,11-dihydro-5H-dibenzo[a,d]cyclohept-Z-en-2-ol hydrochloride salt (99 mg). 5-[3-Dimethylamino-propylidene]-10,11-dihydro-5H-dibenzo[a,d]cyclohept-E-en-2-ol hydrochloride salt: $^1$H NMR (d$_6$-DMSO, 250 MHz): 10.34 (1H, bs), 7.05-7.29 (5H, m), 6.57 (1H, dd), 6.47 (1H, d), 5.69 (1H, t), 3.13 (4H, bs), 2.74 (7H, m), 2.38 (3H, m). 5-[3-dimethylamino-propylidene]-10,11-dihydro-5H-dibenzo[a,d]cyclohept-Z-en-2-ol hydrochloride salt: $^1$H NMR (d$_6$-DMSO, 250 MHz): 10.34 (1H, bs), 7.05-7.25 (4H, m), 6.93 (1H, d), 6.64 (2H, m), 5.70 (1H, t), 3.13 (4H, m), 2.74 (7H, m), 2.38 (3H, m).

Preparation of 5-[3-Dimethylamino-propylidene]-10, 11-dihydro-2-OmPEG6-5H-dibenzo[a,d]cycloheptene (18)

5-[3-Dimethylamino-propylidene]-10,11-dihydro-5H-dibenzo[a,d]cyclohepten-2-ol (17) (20 mg, 60 umol) and potassium carbonate (20 mg, 145 umol) were dissolved in 500 uL acetonitrile. The solution was stirred and mPEG$_6$-OTs (40 mg, 89 umol) was added. The reaction was then heated to 80° C. By LC-MS, the reaction is observed to convert to 5-[3-Dimethylamino-propylidene]-10,11-dihydro-2-OmPEG6-5Hdibenzo[a,d]cycloheptene. ESI MS m/z 573.0 (M+H)$^+$.

Additional compounds of the present disclosure may be prepared using the schemes detailed above and the abilities of one of skill in the art.

EXAMPLE 20

Binding Affinity to Human Norepinephrine Transporter (hNET)

The binding affinities of certain compounds disclosed herein to the hNET were measured using competitive radioligand displacement assays in membranes prepared from MDCK cells that express the human norepinephrine transporter. Competition binding experiments were conducted by incubating hNET membranes with [$^3$H] Nisoxetine (2 nM), in the presence of increasing concentrations of test compounds. Incubations were carried out at 4° C. for 60 minutes in buffer containing 50 mM Tris HCl, 120 mM NaCl and 5 mM KCl (pH 7.4). The binding reaction was terminated by rapid filtration, membranes were washed and membrane-bound radioactivity was measured using a scintillation counter. Non-specific binding was measured in the presence of excess (10 μM) clomipramine as the unlabelled ligand and this value was subtracted from the total binding to yield the specific binding at each test compound concentration.

IC$_{50}$ values were obtained from non-linear regression analysis of concentration-versus specific binding plots. K$_i$ values were calculated from the IC$_{50}$ values using the Cheng Prusoff correction and experimentally determined IQ values for the radioligand under these assay conditions.

EXAMPLE 21

Sodium Channel Assay

The effect of compounds disclosed herein on sodium channels may be evaluated in vitro to determine their blocking properties using the whole-cell patch clamp method in isolated cardiac (human atrial myocytes) and neuronal (rat dorsal root ganglion) cells. The example below refers to a sodium channel assay using neuronal cells.

Electrophysiologic patch clamp recordings of the sodium current in isolated rat dorsal root ganglion (DRG) cells were used to measure the sodium channel blocking properties of certain compounds disclosed herein. DRG cells were isolated according to the method of Blair and Bean (*J Neurosci,* 22: pp. 10277-10290, 2002) and plated on treated glass coverslips. For measuring the sodium current, cells were perfused with an external solution that consists of (in mmol/L): 115 TMA chloride, 10 NaCl, 5 CsCl, 1.8 CaCl2, 1.2 MgCl$_2$, 10 HEPES, 11 dextrose, pH adjusted to 7.4 with TMA-OH. The chemical composition of the internal solution was (in mmol/L): 115 CsF, 20 CsCl, 10 NaF, 10 HEPES, 5 EGTA; pH adjusted to 7.2 with CsOH. Currents were measured using the whole-cell variant of the patch clamp method (Crumb & Clarkson, *Biophysical Journal,* 57(3): 589, 1990). An Axopatch 1-B amplifier (Axon Instruments, Foster City, Calif.) was used for whole-cell voltage clamping. Creation of voltage clamp pulses and data acquisition were controlled by a PC running pClamp software (version 9.2, Axon Instruments). I$_{Na}$ was elicited by a 40 ms pulse to −20 mV from a holding potential of −65 mV. Pacing rates of 0.1 and 3 Hz were examined. Additional experiments were performed in the presence of 500 nM tetrodotoxin in the batch solution to isolate and characterize the tetrodotoxin-resistant component of the total sodium current. Four concentrations of each test compound were added to the cell in a cumulative manner starting with the lowest test concentration. Each cell served as its own control and data are presented as % reduction of current amplitude achieved in the presence of drug. A non-linear curve fitting routine was utilized to fit a three-parameter Hill equation to the results using MicroCal Origin, version 6.0 software. The equation was:

$$y = V_{max} \frac{x^n}{k^n + x^n}$$

where k, and n are unconstrained variables (V$_{max}$=100).

EXAMPLE 22

In Vitro Effect on hERG Channels

Electrophysiological measurements of hERG current were made in vitro to assess the hERG block produced by certain compounds disclosed herein. hERG currents were measured in HEK cells expressing the cloned human hERG channel using the whole-cell variant of the patch clamp method. Experiments were performed at 37±1° C. An Axopatch 1-B amplifier (Axon Instruments, Foster City, Calif.) was used for whole-cell voltage clamping. Creation of voltage clamp pulses and data acquisition was controlled by a PC running pClamp software (version 9.2, Axon Instruments). After rupture of the cell membrane (entering whole-cell mode), current kinetics and amplitudes were allowed to stabilize for 3-5 minutes as the cell was dialyzed with internal solution and paced at 0.1 Hz. Cells were depolarized to +10 mV for 500 ms from a holding potential of −75 mV and peak hERG current was measured as the maximum outward deflection of the tail current elicited upon return to −40 mV (pacing rate=0.1 Hz). Four concentrations of each test compound were added to the cell in a cumulative manner starting with the lowest test concentration. Each cell served as its own control and data are presented as % reduction of current amplitude achieved in the presence of drug.

A nonlinear curve fitting routine was utilized to fit a three-parameter Hill equation to the results using MicroCal Origin, version 6.0 software. The equation was:

$$y = V_{max} \frac{x^n}{k^n + x^n}$$

where k, and n are unconstrained variables ($V_{max}$=100).

The data collected by testing certain compounds of the present disclosure according to Examples 20-22 is summarized in Tables 1 to 3 below. The data suggests that several compounds of the present invention retain binding affinity at the human norpepinephrine transporter (e.g. within 10-fold of amitriptyline). While some loss in the binding affinity to the NET transporter was observed, certain compounds of the present disclosure showed a reduction in their potency of hERG block when compared to amitriptyline. Since certain tricyclic compounds, e.g. tricyclic antidepressants, are often associated with cardiovascular toxicities, the reduction in hERG block observed for certain compounds of the present disclosure could lead to an improved cardiovascular safety profile in vivo for those compounds.

TABLE 1

| Compound Name | NET binding, Ki, μM | INa, DRG, 3 HZ, IC50, μM | IhERG, 0.1 HZ, IC50, μM |
|---|---|---|---|
| amitriptylene | 0.06 | 7.1 | 3.5 |
| (Z)-5-(3-(dimethylamino)propylidene)-10,11-dihydro-5H-dibenzo[a,d][7]annulen-2-ol | 0.5 | 14.9 | 1.6 |
| (E)-5-(3-(dimethylamino)propylidene)-10,11-dihydro-5H-dibenzo[a,d][7]annulen-2-ol | 0.16 | | |
| 5-(3-Dimethylamino-propylidene)-10,11-dihydro-5H-dibenzo[a,d]cyclohept-E-en-2-OmPEG4 | 60.8 | 6.8 | 5.8 |
| 5-(3-Dimethylamino-propylidene)-10,11-dihydro-5H-dibenzo[a,d]cyclohept-E-en-2-OmPEG6 | 35.5 | 16.3 | 61.5 |
| 5-(3-Dimethylamino-propylidene)-10,11-dihydro-5H-dibenzo[a,d]cyclohept-E-en-2-OmPEG8 | 62.9 | 23.4 | 2.2 |
| 5-(3-Dimethylamino-propylidene)-10,11-dihydro-5H-dibenzo[a,d]cyclohept-Z-en-2-OmPEG4 | 21.2 | 12.8 | 24.9 |
| 5-(3-Dimethylamino-propylidene)-10,11-dihydro-5H-dibenzo[a,d]cyclohept-Z-en-2-OmPEG6 | 37.7 | 12.4 | 8.1 |
| 5-(3-Dimethylamino-propylidene)-10,11-dihydro-5H-dibenzo[a,d]cyclohept-Z-en-2OmPEG8 | 646 | 16.9 | 26.4 |

TABLE 2

| Compound Name | NET binding, Ki, μM | INa, DRG, 3 HZ, IC50, μM | IhERG, 0.1 HZ, IC50, μM |
|---|---|---|---|
| Amitriptyline | 0.103 | 7.1 | 3.5 |
| (R)-5-(3-dimethylamino-propylidene)-10,11-dihydro-5H-dibenzo[a,d]cyclohept-E-en-10-ol | 2.53 | 6.2 | 18.0 |
| (R)-5-(3-dimethylamino-propylidene)-10-OmPEG$_1$-10,11-dihydro-5H-dibenzo[a,d]cyclohept-E-ene trifluoroacetate salt | 4.45 | | 12.1 |
| (R)-5-(3-dimethylamino-propylidene)-10-OmPEG$_2$-10,11-dihydro-5H-dibenzo[a,d]cyclohept-E-ene trifluoroacetate salt | 49.1 | | 14 |
| (R)-5-(3-dimethylamino-propylidene)-10-OmPEG$_4$-10,11-dihydro-5H-dibenzo[a,d]cyclohept-E-ene trifluoroacetate salt | 28.14 | 21.3 | 39.9 |
| (R)-5-(3-dimethylamino-propylidene)-10-OmPEG$_6$-10,11-dihydro-5H-dibenzo[a,d]cyclohept-E-ene trifluoroacetate salt | 60.4 | 8.1 | 37.9 |

TABLE 2-continued

| Compound Name | NET binding, Ki, µM | INa, DRG, 3 HZ, IC50, µM | IhERG, 0.1 HZ, IC50, µM |
| --- | --- | --- | --- |
| (R)-5-(3-dimethylamino-propylidene)-10-OmPEG8-10,11-dihydro-5H-dibenzo[a,d]cyclohept-E-ene trifluoroacetate salt | 13.5 | 21.2 | 55.9 |
| (S)-5-(3-dimethylamino-propylidene)-10,11-dihydro-5H-dibenzo[a,d]cyclohept-E-en-10-ol | 0.34 | 16.6 | 23.2 |
| (S)-5-(3-dimethylamino-propylidene)-10-OmPEG4-10,11-dihydro-5H-dibenzo[a,d]cyclohept-E-ene trifluoroacetate salt | 12.6 | 39.4 | 24.8 |
| (S)-5-(3-dimethylamino-propylidene)-10-OmPEG6-10,11-dihydro-5H-dibenzo[a,d]cyclohept-E-ene trifluoroacetate salt | 14.2 | 8.5 | 36.0 |
| (S)-5-(3-dimethylamino-propylidene)-10-OmPEG8-10,11-dihydro-5H-dibenzo[a,d]cyclohept-E-ene trifluoroacetate salt | 14.03 | 71.6 | >100 |

TABLE 3

| Compound Name | NET binding, Ki, µM | INa, DRG, 3 HZ, IC50, µM | IhERG, 0.1 HZ, IC50, µM |
| --- | --- | --- | --- |
| Amitriptyline | 0.079 | | 3.5 |
| (R)-5-(3-dimethylamino-propylidene)-10,11-dihydro-5H-dibenzo[a,d]cyclohept-Z-en-10-ol | 6.28 | | 4.1 |
| (S)-5-(3-dimethylamino-propylidene)-10,11-dihydro-5H-dibenzo[a,d]cyclohept-Z-en-10-ol | 0.97 | | 7.2 |
| (R)-5-(3-dimethylamino-propylidene)-10-OmPEG4-10,11-dihydro-5H-dibenzo[a,d]cyclohept-Z-ene trifluoroacetate salt | 30.6 | | 21.5 |
| (R)-5-(3-dimethylamino-propylidene)-10-OmPEG6-10,11-dihydro-5H-dibenzo[a,d]cyclohept-Z-ene trifluoroacetate salt | 31.3 | | 18.9 |
| (R)-5-(3-dimethylamino-propylidene)-10-OmPEG8-10,11-dihydro-5H-dibenzo[a,d]cyclohept-Z-ene trifluoroacetate salt | 4.37 | | >100 |
| (S)-5-(3-dimethylamino-propylidene)-10-OmPEG4-10,11-dihydro-5H-dibenzo[a,d]cyclohept-Z-ene trifluoroacetate salt | 27.4 | | 11.5 |
| (S)-5-(3-dimethylamino-propylidene)-10-OmPEG6-10,11-dihydro-5H-dibenzo[a,d]cyclohept-Z-ene trifluoroacetate salt | 22.1 | | 38.3 |
| (S)-5-(3-dimethylamino-propylidene)-10-OmPEG8-10,11-dihydro-5H-dibenzo[a,d]cyclohept-Z-ene trifluoroacetate salt | 2.99 | | 32.8 |

EXAMPLE 23

Histamine Receptor Binding Assay

The receptor binding affinities of compounds disclosed herein may be evaluated using radioligand binding assays in membranes prepared from CHO cells that express the recombinant human H1, H2, H3 or H4 histamine receptors.

Competition binding experiments are conducted by incubating membranes with a fixed concentration of radioligand in the presence of variable concentrations of test compounds. The radioligands used are specific for each receptor subtype and assay conditions are described in Table 4. Following incubations, the membranes are washed and the bound radioactivity is measured. Non-specific binding is measured in the presence of excess unlabelled ligand; this value is subtracted from the total binding yielding the specific binding at each test compound concentration.

$IC_{50}$ values are obtained from non-linear regression analysis of dose-response curves and are calculated only for those compounds that show >50% inhibition of binding at the highest concentration tested. $K_i$ is obtained using the Cheng Prusoff correction using experimental $K_i$ values that are determined under the same assay conditions.

TABLE 4

Assay Conditions
Receptor source: Human recombinant CHO or CHO K1 cells expressing individual histamine H1, H2, H3, or H4 receptors.

| Receptor | Radioligand | Non-specific binding | Methods | Test Concentration |
| --- | --- | --- | --- | --- |
| Histamine H1 | [$^3$H]-Pyrilamine (1.2 nM) | Pyrilamine (1 µM) | Reaction in 50 mM Tris-HCl (pH 7.4), 2 mM $MgCl_2$, 100 mM NaCl and 250 mM Sucrose at 25° C. for 3 h. | 0.01, 0.1, 0.3, 1, 3, 10, 30, 100 nM, 3, 30 µM |
| Histamine H2 | [$^{125}$I]-Aminopotentidine (0.1 nM) | Tiotidine (3 µM) | Reaction in 50 mM phosphate (pH 7.4) at 25° C. for 2 h. | 0.01, 0.1, 0.3, 1, 3, 10, 30, 100 nM, 3, 30 µM |
| Histamine H3 | [$^3$H]-R(−)-α-Methyl-histamine (3 nM) | R(−)-α-Methyl-histamine (1 µM) | Reaction in 50 mM Tris-HCl (pH 7.4), 5 mM $MgCl_2$, 0.04% BSA at 25° C. for 1.5 h. | 0.01, 0.1, 0.3, 1, 3, 10, 30, 100 nM, 3, 30 µM |

TABLE 4-continued

Assay Conditions
Receptor source: Human recombinant CHO or CHO K1 cells expressing individual histamine H1, H2, H3, or H4 receptors.

| Receptor | Radioligand | Non-specific binding | Methods | Test Concentration |
|---|---|---|---|---|
| Histamine H4 | [³H]-Histamine (8.2 nM) | Histamine (1 μM) | Reaction in 50 mM Tris-HCl (pH 7.4), 1.25 mM EDTA at 25° C. for 1.5 h. | 0.01, 0.1, 0.3, 1, 3, 10, 30, 100 nM, 3, 30 μM |

EXAMPLE 24

Muscarinic Receptor Binding Assay

The receptor binding affinities of compounds disclosed herein and their non-conjugated counterparts may be evaluated using radioligand binding assays in membranes prepared from CHO cells that express the recombinant human M1, M2, M3, M4 or M5 muscarinic acetylcholine receptors. Competition binding experiments are conducted by incubating membranes with a fixed concentration of radioligand in the presence of variable concentrations of test compounds. ³H—N-Methylscopolamine at 0.8 nM is used as the radioligand for all receptor subtypes. Incubations are carried out for 2 hours at 25° C. in buffer containing 50 mM Tris HCl, 10 mM $MgCl_2$ and 1 mM EDTA. Following incubations, the membranes are washed and the bound radioactivity is measured. Non-specific binding is measured in the presence of excess Atropine as the cold ligand and subtraction of this value from the total binding yields the specific binding at each test compound concentration. $IC_{50}$ values are obtained from non-linear regression analysis of dose-response curves and were calculated only for those compounds that show >50% inhibition of binding at the highest concentration tested. Ki is obtained using the Cheng Prusoff correction using Kd values that are experimentally determined previously under these assay conditions.

EXAMPLE 25

Analgesic Assay

An analgesic assay may be used to determine whether a given compound can reduce and/or prevent visceral pain in mice.

The assay utilizes CD-1 male mice (5-8 mice per group), each mouse being approximately 0.015-0.030 kg on the study day. Mice are treated according to standard protocols.

Mice are given a single "pretreatment" dose of a compound lacking covalent attachment of a water-soluble, non-peptidic oligomer, a corresponding version comprising the compound covalently attached to a water-soluble, non-peptidic oligomer, or control solution (IV, SC, IP or orally) thirty minutes prior to the administration of the acetic acid solution. The animal is given an IP injection of an irritant (acetic acid) that induces "writhing" which may include: contractions of the abdomen, twisting and turning of the trunk, arching of the back and the extension of the hindlimbs. Mice are given a single IP injection (0.1 mL/10 g bodyweight) of a 0.5% acetic acid solution. After the injection the animals are returned to their observation enclosure and their behavior is observed. Contractions are counted between 0 and 20 minutes after the injection. The animals are used once. Each tested article is dosed at 1, 3 and 10 mg/kg (n=5 animals/dose).

What is claimed is:

1. A compound of formula:

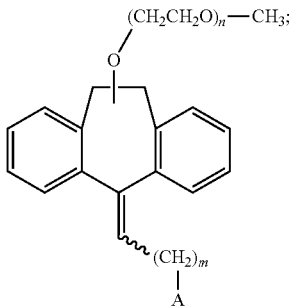

or at least one pharmaceutically acceptable salt thereof;
wherein:
    n is an integer from 1 to 30;
    m is an integer from 1 to 4; and
    A is selected from —NHCH₃ and —N(CH₃)₂.

2. The compound of claim 1, wherein m is 2.
3. The compound of claim 2, wherein A is —N(CH₃)₂.
4. The compound of claim 3, of the formula:

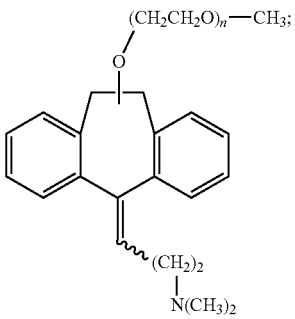

or at least one pharmaceutically acceptable salt thereof.

5. The compound of claim 3, of the formula:

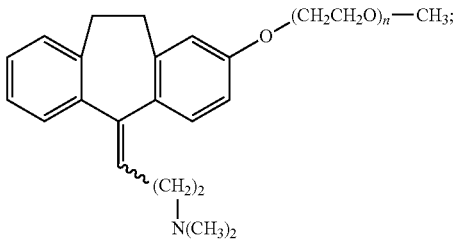

or at least one pharmaceutically acceptable salt thereof.

6. The compound of claim 4, of the formula:

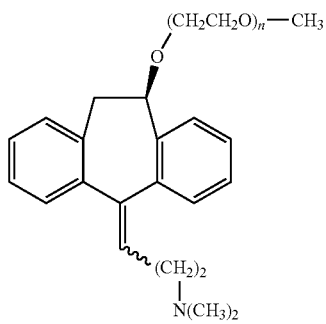

or at least one pharmaceutically acceptable salt thereof.

7. The compound of claim 4, of the formula:

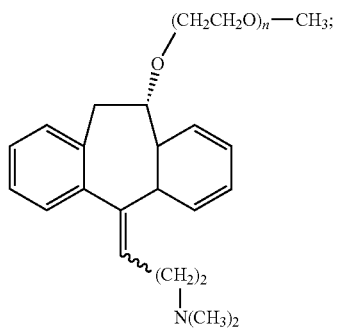

or at least one pharmaceutically acceptable salt thereof.

8. The compound of claim 4, wherein the compound is the (E) isomer.

9. The compound of claim 4, wherein the compound is the (Z) isomer.

10. The compound of claim 4, wherein n is an integer from 1 to 10.

11. A compound, or at least one pharmaceutically acceptable salt thereof, selected from:
(R)-5-(3-dimethylamino-propylidene)-10-OmPEG$_4$-10,11-dihydro-5H-dibenzo[a,d]cyclohept-E-ene;
(R)-5-(3-dimethylamino-propylidene)-10-OmPEG$_1$-10,11-dihydro-5H-dibenzo[a,d]cyclohept-E-ene;
(R)-5-(3-dimethylamino-propylidene)-10-OmPEG$_2$-10,11-dihydro-5H-dibenzo[a,d]cyclohept-E-ene;
(R)-5-(3-dimethylamino-propylidene)-10-OmPEG$_6$-10,11-dihydro-5H-dibenzo[a,d]cyclohept-E-ene;
(R)-5-(3-dimethylamino-propylidene)-10-OmPEG$_8$-10,11-dihydro-5H-dibenzo[a,d]cyclohept-E-ene;
(S)-5-(3-dimethylamino-propylidene)-10-OmPEG$_4$-10,11-dihydro-5H-dibenzo[a,d]cyclohept-E-ene;
(S)-5-(3-dimethylamino-propylidene)-10-OmPEG$_6$-10,11-dihydro-5H-dibenzo[a,d]cyclohept-E-ene;
(S)-5-(3-dimethylamino-propylidene)-10-OmPEG$_8$-10,11-dihydro-5H-dibenzo[a,d]cyclohept-E-ene;
(R)-5-(3-dimethylamino-propylidene)-10-OmPEG$_4$-10,11-dihydro-5H-dibenzo[a,d]cyclohept-Z-ene;
(R)-5-(3-dimethylamino-propylidene)-10-OmPEG$_6$-10,11-dihydro-5H-dibenzo[a,d]cyclohept-Z-ene;
(R)-5-(3-dimethylamino-propylidene)-10-OmPEG$_8$-10,11-dihydro-5H-dibenzo[a,d]cyclohept-Z-ene;
(S)-5-(3-dimethylamino-propylidene)-10-OmPEG$_4$-10,11-dihydro-5H-dibenzo[a,d]cyclohept-Z-ene;
(S)-5-(3-dimethylamino-propylidene)-10-OmPEG$_6$-10,11-dihydro-5H-dibenzo[a,d]cyclohept-Z-ene;
(S)-5-(3-dimethylamino-propylidene)-10-OmPEG$_8$-10,11-dihydro-5H-dibenzo[a,d]cyclohept-Z-ene;
5-(3-Dimethylamino-propylidene)-10,11-dihydro-5H-dibenzo[a,d]cyclohept-E-en-2-OmPEG$_4$;
5-(3-Dimethylamino-propylidene)-10,11-dihydro-5H-dibenzo[a,d]cyclohept-Z-en-2-OmPEG$_4$;
5-(3-Dimethylamino-propylidene)-10,11-dihydro-5H-dibenzo[a,d]cyclohept-E-en-2-OmPEG$_6$;
5-(3-Dimethylamino-propylidene)-10,11-dihydro-5H-dibenzo[a,d]cyclohept-Z-en-2-OmPEG$_6$;
5-(3-Dimethylamino-propylidene)-10,11-dihydro-5H-dibenzo[a,d]cyclohept-E-en-2-OmPEG$_8$; and
5-(3-Dimethylamino-propylidene)-10,11-dihydro-5H-dibenzo[a,d]cyclohept-Z-en-2-OmPEG$_8$.

12. A composition comprising a compound of claim 1, and optionally, a pharmaceutically acceptable excipient.

13. A composition of matter comprising a compound of claim 1, wherein the compound is present in a dosage form.

14. The compound of claim 5, wherein the compound is the (E) isomer.

15. The compound of claim 5, wherein the compound is the (Z) isomer.

16. The compound of claim 5, wherein n is an integer from 1 to 10.

17. A composition comprising a compound of claim 11, and optionally, a pharmaceutically acceptable excipient.

18. A composition of matter comprising a compound of claim 11, wherein the compound is present in a dosage form.

* * * * *